(12) United States Patent
Hepworth et al.

(10) Patent No.: US 11,865,246 B2
(45) Date of Patent: Jan. 9, 2024

(54) APPARATUS FOR GENERATING AN INHALABLE MEDIUM

(71) Applicant: NICOVENTURES TRADING LIMITED, London (GB)

(72) Inventors: Richard Hepworth, London (GB); Dominic Woodcock, London (GB); Joseph Sutton, London (GB); Sharon Goodall, London (GB)

(73) Assignee: NICOVENTURES TRADING LIMITED, London (GB)

( * ) Notice: Subject to any disclaimer, the term of this patent is extended or adjusted under 35 U.S.C. 154(b) by 508 days.

(21) Appl. No.: 15/553,785

(22) PCT Filed: Feb. 29, 2016

(86) PCT No.: PCT/EP2016/054232
§ 371 (c)(1),
(2) Date: Aug. 25, 2017

(87) PCT Pub. No.: WO2016/135342
PCT Pub. Date: Sep. 1, 2016

(65) Prior Publication Data
US 2018/0027882 A1    Feb. 1, 2018

(30) Foreign Application Priority Data

Feb. 27, 2015 (GB) ..................................... 1503411
Oct. 2, 2015 (GB) ..................................... 1517470

(51) Int. Cl.
*A61M 11/04* (2006.01)
*A61M 15/06* (2006.01)
(Continued)

(52) U.S. Cl.
CPC .......... *A61M 11/041* (2013.01); *A24F 40/42* (2020.01); *A61M 15/06* (2013.01); *A24F 40/10* (2020.01);
(Continued)

(58) Field of Classification Search
CPC .......... A24F 40/42; A24F 40/20; A24F 40/30; A24F 40/95; A24F 47/004; A24F 47/008;
(Continued)

(56) References Cited

U.S. PATENT DOCUMENTS

| 4,083,372 A | 4/1978 | Boden |
| 4,284,089 A | 8/1981 | Ray |

(Continued)

FOREIGN PATENT DOCUMENTS

| AT | 507187 A4 | 3/2010 |
| AT | 507187 B1 | 3/2010 |

(Continued)

OTHER PUBLICATIONS

Japanese Office Action, Application No. 2017-545230, dated Oct. 30, 2019, 4 pages.
(Continued)

*Primary Examiner* — Samchuan C Yao
*Assistant Examiner* — Nathan M Le
(74) *Attorney, Agent, or Firm* — Patterson, Thuente PA

(57) ABSTRACT

Presented are apparatus and methods for generating an inhalable medium. An apparatus including a container holding a liquid, a heater for volatizing the liquid, and a plurality of discrete material elements is used. The liquid held in the container is volatized. At least one of a vapor and an aerosol formed by the volatized liquid is passed through one or more of the plurality of discrete material elements. One or more constituents of the one or more of the plurality of discrete
(Continued)

material elements is thereby entrained in the at least one of a vapor and an aerosol to produce the inhalable medium.

18 Claims, 7 Drawing Sheets

(51) Int. Cl.
  *A24F 40/42* (2020.01)
  *A24F 40/10* (2020.01)
  *A24F 40/20* (2020.01)

(52) U.S. Cl.
  CPC ...... *A24F 40/20* (2020.01); *A61M 2205/3653* (2013.01)

(58) Field of Classification Search
  CPC ............ A61M 11/042; A61M 15/0003; A61M 15/0028
  See application file for complete search history.

(56) References Cited

U.S. PATENT DOCUMENTS

| | | | |
|---|---|---|---|
| 4,756,318 A | 7/1988 | Clearman | |
| 4,907,606 A | 3/1990 | Lilja et al. | |
| 4,913,169 A | 4/1990 | Templeton | |
| 5,027,836 A | 7/1991 | Shannon | |
| 5,027,839 A | 7/1991 | Appell | |
| 5,105,834 A | 4/1992 | Saintsing et al. | |
| 5,115,820 A | 5/1992 | Hauser | |
| 5,203,355 A | 4/1993 | Clearman | |
| 5,327,915 A | 7/1994 | Porenski | |
| 5,613,505 A * | 3/1997 | Campbell ............ A24F 47/008 131/194 |
| 5,820,967 A | 10/1998 | Gadkaree | |
| 5,950,619 A | 9/1999 | van der Linden et al. | |
| 6,095,558 A | 8/2000 | Bayer | |
| 6,814,786 B1 | 11/2004 | Zhuang | |
| 6,988,496 B1 | 1/2006 | Eicher et al. | |
| 7,160,366 B2 | 1/2007 | Blackburn | |
| 7,699,052 B2 | 4/2010 | Schiewe et al. | |
| 8,536,606 B2 | 9/2013 | Kim | |
| 8,833,364 B2 | 9/2014 | Buchberger | |
| 8,997,753 B2 | 4/2015 | Li | |
| 9,259,031 B2 | 2/2016 | Branton | |
| D761,998 S | 7/2016 | Pinder | |
| D768,915 S | 10/2016 | Wright | |
| 9,456,632 B2 | 10/2016 | Hon | |
| D782,728 S | 3/2017 | Pinder | |
| D782,729 S | 3/2017 | Wright | |
| D805,684 S | 12/2017 | Thuery | |
| 9,894,930 B2 | 2/2018 | Bonici et al. | |
| D815,342 S | 4/2018 | Sutton | |
| D818,635 S | 5/2018 | Pinder | |
| D818,638 S | 5/2018 | Wright | |
| D825,099 S | 8/2018 | Wright | |
| D825,103 S | 8/2018 | Wright | |
| 10,226,077 B2 | 3/2019 | Matsumoto et al. | |
| 10,375,996 B2 | 8/2019 | Aoun | |
| 10,426,199 B2 | 10/2019 | Turner et al. | |
| 2004/0194792 A1 | 10/2004 | Zhuang | |
| 2005/0133051 A1 | 6/2005 | Luan | |
| 2005/0133054 A1 | 6/2005 | Fournier | |
| 2006/0144412 A1 | 7/2006 | Mishra | |
| 2006/0201524 A1 | 9/2006 | Zhang | |
| 2007/0023056 A1 | 2/2007 | Cantrell | |
| 2007/0215168 A1 | 9/2007 | Banerjee | |
| 2008/0092912 A1 | 4/2008 | Robinson | |
| 2008/0110470 A1 | 5/2008 | Zhang | |
| 2008/0241255 A1 * | 10/2008 | Rose ................... A24F 47/004 424/489 |
| 2010/0024834 A1 | 2/2010 | Oglesby et al. | |
| 2011/0088707 A1 | 4/2011 | Hajaligol | |
| 2011/0226236 A1 * | 9/2011 | Buchberger ......... A61K 31/465 128/200.23 |
| 2012/0006342 A1 | 1/2012 | Rose et al. | |
| 2012/0006346 A1 * | 1/2012 | Inagaki ................ A61M 11/042 131/329 |
| 2012/0042885 A1 | 2/2012 | Stone | |
| 2012/0199663 A1 | 8/2012 | Weihua | |
| 2012/0255567 A1 * | 10/2012 | Rose ..................... A24F 47/00 131/273 |
| 2012/0312314 A1 | 12/2012 | Plakidis et al. | |
| 2012/0318882 A1 | 12/2012 | Abehasera | |
| 2013/0014772 A1 | 1/2013 | Liu | |
| 2013/0056013 A1 | 3/2013 | Terry | |
| 2013/0133675 A1 | 5/2013 | Yasuhiro | |
| 2013/0160779 A1 | 6/2013 | Chida et al. | |
| 2013/0160780 A1 * | 6/2013 | Matsumoto ............. B65B 1/20 131/329 |
| 2013/0192616 A1 | 8/2013 | Tucker | |
| 2013/0192620 A1 | 8/2013 | Tucker | |
| 2013/0298905 A1 * | 11/2013 | Levin .................... A24F 47/008 128/202.21 |
| 2013/0333700 A1 | 12/2013 | Buchberger | |
| 2014/0048085 A1 | 2/2014 | Cox | |
| 2014/0076340 A1 | 3/2014 | Kizer et al. | |
| 2014/0123989 A1 | 5/2014 | Lamothe | |
| 2014/0159250 A1 | 6/2014 | Nickerson | |
| 2014/0166029 A1 * | 6/2014 | Weigensberg .......... A24F 40/30 131/329 |
| 2014/0190502 A1 | 7/2014 | Liu | |
| 2014/0238422 A1 | 8/2014 | Plunkett et al. | |
| 2014/0261486 A1 | 9/2014 | Potter | |
| 2014/0299125 A1 | 10/2014 | Buchberger | |
| 2014/0305449 A1 | 10/2014 | Plojoux | |
| 2014/0356607 A1 | 12/2014 | Woodcock | |
| 2015/0027454 A1 | 1/2015 | Li | |
| 2015/0128973 A1 | 5/2015 | Li et al. | |
| 2015/0196059 A1 | 7/2015 | Li | |
| 2015/0257447 A1 | 9/2015 | Sullivan | |
| 2015/0264979 A1 | 9/2015 | Thorens et al. | |
| 2015/0342256 A1 | 12/2015 | Chen | |
| 2015/0374035 A1 | 12/2015 | Sanchez et al. | |
| 2016/0020224 A1 | 1/2016 | Kawamura et al. | |
| 2016/0073692 A1 | 3/2016 | Alarcon et al. | |
| 2016/0120224 A1 | 5/2016 | Mishra | |
| 2016/0135505 A1 | 5/2016 | Li et al. | |
| 2016/0143360 A1 | 5/2016 | Sanchez et al. | |
| 2016/0174610 A1 | 6/2016 | Kuczaj | |
| 2016/0205992 A1 | 7/2016 | Bell et al. | |
| 2016/0227837 A1 | 8/2016 | Hammel et al. | |
| 2016/0255879 A1 | 9/2016 | Paprocki | |
| 2016/0324216 A1 | 11/2016 | Li | |
| 2016/0353801 A1 | 12/2016 | Zinovik et al. | |
| 2017/0042221 A1 | 2/2017 | England | |
| 2017/0086506 A1 | 3/2017 | Rado | |
| 2017/0095624 A1 * | 4/2017 | Davidson ............. A61K 31/352 |
| 2017/0143038 A1 | 5/2017 | Dickens | |
| 2017/0156402 A1 | 6/2017 | Liu | |
| 2017/0238612 A1 * | 8/2017 | Daryani ................. A24F 40/30 |
| 2017/0251727 A1 | 9/2017 | Nielsen | |
| 2017/0280769 A1 | 10/2017 | Li et al. | |
| 2017/0319799 A1 | 11/2017 | Yamada et al. | |
| 2017/0347706 A1 | 12/2017 | Aoun et al. | |
| 2018/0027882 A1 | 2/2018 | Hepworth | |
| 2018/0235276 A1 | 8/2018 | Zuleta et al. | |
| 2018/0279667 A1 | 10/2018 | McAdam et al. | |
| 2018/0279678 A1 | 10/2018 | Hepworth et al. | |
| 2018/0325174 A1 | 11/2018 | Sutton | |
| 2018/0360122 A1 | 12/2018 | Aoun | |
| 2018/0368478 A1 | 12/2018 | Golovanova et al. | |
| 2019/0230990 A1 | 8/2019 | Hepworth | |
| 2019/0254343 A1 | 8/2019 | Hepworth et al. | |
| 2019/0320718 A1 | 10/2019 | Yilmaz et al. | |
| 2019/0320725 A1 | 10/2019 | England | |

FOREIGN PATENT DOCUMENTS

| | | |
|---|---|---|
| CA | 885796 | 11/1971 |
| CA | 2330782 | 7/2002 |
| CA | 2925645 A1 | 4/2015 |
| CA | 2940842 A1 | 9/2015 |

(56) References Cited

FOREIGN PATENT DOCUMENTS

| | | |
|---|---|---|
| CN | 1054887 | 10/1991 |
| CN | 101433818 | 5/2009 |
| CN | 101557728 | 10/2009 |
| CN | 102264249 A | 11/2011 |
| CN | 102834027 | 12/2012 |
| CN | 103315402 | 9/2013 |
| CN | 103892467 | 7/2014 |
| CN | 203762287 | 8/2014 |
| CN | 104068474 A | 10/2014 |
| CN | 104284606 | 1/2015 |
| CN | 104302197 A | 1/2015 |
| CN | 204273243 U | 4/2015 |
| CN | 204317492 U | 5/2015 |
| CN | 104770876 A | 7/2015 |
| CN | 204653789 | 9/2015 |
| CN | 104957779 A | 10/2015 |
| CN | 105357995 A | 2/2016 |
| CN | 105394816 A | 3/2016 |
| CN | 105792688 A | 7/2016 |
| CN | 105962423 A | 9/2016 |
| DE | 2940535 | 10/1980 |
| EA | 019736 B1 | 5/2014 |
| EP | 0 174 645 A2 | 3/1986 |
| EP | 0254551 | 1/1988 |
| EP | 0 307 118 | 8/1988 |
| EP | 0305788 A1 | 3/1989 |
| EP | 0 352 106 A2 | 1/1990 |
| EP | 0 535 695 A2 | 4/1993 |
| EP | 0585016 | 3/1994 |
| EP | 845220 | 6/1998 |
| EP | 1468618 A1 | 10/2004 |
| EP | 2489391 | 8/2012 |
| EP | 2625974 A1 | 8/2013 |
| EP | 2625975 | 8/2013 |
| EP | 2399637 B1 | 10/2014 |
| EP | 2787848 A1 | 10/2014 |
| EP | 2989912 A1 | 3/2016 |
| EP | 3127443 | 2/2017 |
| GB | 2529201 A | 2/2016 |
| JP | S4742449 Y1 | 12/1972 |
| JP | S488231 U | 1/1973 |
| JP | S488231 B1 | 3/1973 |
| JP | S48008231 B | 3/1973 |
| JP | S60237982 A | 11/1985 |
| JP | S63193499 U | 12/1988 |
| JP | 06064983 | 3/1994 |
| JP | 2001120250 A | 5/2001 |
| JP | 2009191148 | 8/2009 |
| JP | 2010506594 A | 3/2010 |
| JP | 2012506263 A | 3/2012 |
| JP | 5247711 | 7/2013 |
| JP | 2013545474 | 12/2013 |
| JP | 2014511175 A | 5/2014 |
| JP | 2014520542 A | 8/2014 |
| JP | 2014 529996 A | 11/2014 |
| JP | 2015504667 | 2/2015 |
| JP | 2015509718 | 4/2015 |
| JP | 5714637 B2 | 5/2015 |
| JP | 2015513393 A | 5/2015 |
| JP | 2017511703 A | 4/2017 |
| JP | 2017-529896 | 10/2017 |
| JP | 2017538398 A | 12/2017 |
| JP | 2018512117 A | 5/2018 |
| JP | 2018512118 A | 5/2018 |
| KR | 20120053521 | 5/2012 |
| KR | 20130052119 A | 5/2013 |
| KR | 20140118982 | 10/2014 |
| KR | 20170125064 A | 11/2017 |
| RU | 122254 U1 | 11/2012 |
| RU | 2528945 C1 | 9/2014 |
| RU | 2570499 C2 | 12/2015 |
| RU | 2576015 C2 | 2/2016 |
| RU | 2587073 C2 | 6/2016 |
| WO | WO 98/28994 | 12/1997 |
| WO | WO 9748293 | 11/1998 |
| WO | WO 9748296 | 11/1998 |
| WO | WO 2001030184 | 5/2001 |
| WO | WO 03008068 | 1/2003 |
| WO | WO 03/034847 A1 | 5/2003 |
| WO | WO-03056949 A1 | 7/2003 |
| WO | WO2004086888 | 10/2004 |
| WO | WO 2004087309 | 10/2004 |
| WO | WO 2006048766 | 5/2006 |
| WO | WO 2006070291 | 7/2006 |
| WO | WO 2006072889 | 7/2006 |
| WO | WO 2006089404 | 8/2006 |
| WO | WO 2006097852 | 9/2006 |
| WO | WO 2006103404 | 10/2006 |
| WO | WO 2006109189 | 10/2006 |
| WO | WO 2007031876 | 3/2007 |
| WO | WO 2007036814 | 4/2007 |
| WO | 2007054167 A1 | 5/2007 |
| WO | WO 2007069093 | 6/2007 |
| WO | WO-2008108889 A1 | 9/2008 |
| WO | 2011034723 A1 | 3/2011 |
| WO | 2011045609 A1 | 4/2011 |
| WO | 2011160788 A1 | 12/2011 |
| WO | WO-2012106739 A1 | 8/2012 |
| WO | 2012134380 A1 | 10/2012 |
| WO | WO-2012168699 A1 | 12/2012 |
| WO | WO 2013034458 | 3/2013 |
| WO | WO 2013/083638 | 6/2013 |
| WO | WO-2013098405 A2 | 7/2013 |
| WO | WO 2013102309 | 7/2013 |
| WO | WO-2013116558 A1 | 8/2013 |
| WO | WO-2013120565 A2 | 8/2013 |
| WO | WO 2013/155645 | 10/2013 |
| WO | WO 2013155645 | 10/2013 |
| WO | WO-2013164705 A1 | 11/2013 |
| WO | WO 2014/116974 | 7/2014 |
| WO | WO 2014116974 | 7/2014 |
| WO | WO 2014/139611 | 9/2014 |
| WO | WO-2014136872 A1 | 9/2014 |
| WO | WO-2014140273 A2 | 9/2014 |
| WO | WO-2014140320 A1 | 9/2014 |
| WO | WO-2014150773 A1 | 9/2014 |
| WO | WO-2014159250 A1 | 10/2014 |
| WO | 2014187763 A1 | 11/2014 |
| WO | 2015038981 A2 | 3/2015 |
| WO | WO 2015/046385 A1 | 4/2015 |
| WO | WO-2015062983 A2 | 5/2015 |
| WO | WO-2015091258 A1 | 6/2015 |
| WO | WO 2015/128499 A1 | 9/2015 |
| WO | WO 2015/179388 A1 | 11/2015 |
| WO | WO-2015188348 A1 | 12/2015 |
| WO | 2016005602 A1 | 1/2016 |
| WO | WO-2016024083 A1 | 2/2016 |
| WO | 2016050244 A1 | 4/2016 |
| WO | WO 2016/062777 | 4/2016 |
| WO | WO 2016062777 | 4/2016 |
| WO | 2016079729 A1 | 5/2016 |
| WO | WO-2016075748 A1 | 5/2016 |
| WO | WO-2016121143 A1 | 8/2016 |
| WO | WO-2016124740 A1 | 8/2016 |
| WO | WO-2016124741 A1 | 8/2016 |
| WO | WO-2016135331 A1 | 9/2016 |
| WO | WO-2016135342 A2 | 9/2016 |
| WO | WO-2016135342 A3 | 10/2016 |
| WO | WO-2016179376 A1 | 11/2016 |
| WO | 2017055584 A1 | 4/2017 |
| WO | 2017068100 A1 | 4/2017 |
| WO | 2018033649 A1 | 2/2018 |
| WO | 2018130391 A1 | 7/2018 |

OTHER PUBLICATIONS

English Translation of Japanese Office Action, Application No. 2018-515290, dated Jan. 21, 2020, 4 pages.
Chinese Office Action and Search Report, Application No. 201680056939.7, dated Feb. 3, 2020, 20 pages.
Chinese Office Action, Application No. 201680024577.3, dated Sep. 12, 2019, 21 pages.

(56) References Cited

OTHER PUBLICATIONS

Chinese Office Action, Application No. 201680024542.X, dated Nov. 12, 2019, 52 pages.
European Communication, Application No. 16709731.0, dated Sep. 30, 2019, 28 pages.
Japanese Office Action, Application No. 2017-522122, dated Feb. 5, 2019, 16 pages.
Translation of Korean Office Action, Application No. 10-2017-7027341, dated Apr. 26, 2019.
European Communication, Application No. 18190846.8, dated Apr. 1, 2020, 5 pages.
European Communication, Application No. 18190846.8, dated Apr. 1, 2020, 13 pages.
Brazilian Office Action, Application No. BR 1120170184460, dated Mar. 23, 2020.
Australian Examination Report, Application No. 2019200330, dated Apr. 14, 2020, 7 pages.
JAC Vapour E-Cigarettes & E-Liquids, Round Rubber Mouth Tips, www.jacapour.com, 2 pages.
International Preliminary Report on Patentability, International Application No. PCT/EP2016/054232, dated Jul. 3, 2017, 10 pages.
International Search Report, International Application No. PCT/EP2016/054232, dated Aug. 24, 2016, 5 pages.
GB Search Report, Application No. GB1517470.9, dated Mar. 21, 2016, 4 pages.
Partial International Search Report, International Application No. PCT/EP2016/054232, dated Jun. 22, 2016, 6 pages.
International Search Report, Application No. PCT/EP2015/074395, dated Feb. 1, 2016, 2 pages.
Application and File History for U.S. Appl. No. 15/553,742, filed Aug. 25, 2017, Inventor: Turner.
Application and File History for U.S. Appl. No. 15/307,074, filed Oct. 27, 2016, Inventor: England.
International Preliminary Report on Patentability, International Application No. PCT/EP2016/054159, dated Jul. 14, 2017, 7 pages.
International Search Report, International Application No. PCT/EP2016/054159, dated Jun. 9, 2016, 3 pages.
Australian Examination Report, Application No. 2015334902, dated Dec. 22, 2017, 3 pages.
Application and File History for U.S. Appl. No. 14/124,637, filed Feb. 7, 2014, Inventor Branton.
Definition of "throughout," the Free Merriam-Webster Dictionary, retrieved from the Internet on Mar. 7, 2015, available at: http://www.merriam-webster.com/dictionary/throughout.
International Search Report and Written Opinion, dated Sep. 17, 2012 for PCT/GB2012/051257, filed Jun. 1, 2012, 7 pages.
Written Opinion of the IPEA, dated May 29, 2013 for PCT/GB2012/051257, filed Jun. 1, 2012.
International Preliminary Report on Patentability, dated Jul. 12, 2013 for PCT/GB2012/051257, filed Jun. 1, 2012, 20 pages.
Australian Examination Report, Application No. 2015334902, dated May 11, 2018, 3 pages.
Canadian Office Action, Application No. 2,963,957, dated Mar. 16, 2018, 4 pages.
Korean Office Action, Application No. 10-2017-7013874, dated Apr. 25, 2018, 7 pages (14 pages with translation).
Application and Filing Receipt for U.S. Appl. No. 16/058,604, filed Aug. 8, 2018, Inventors: Aoun et al.
Chinese Office Action, Application No. 201580023949.5, dated Jul. 2, 2018, 23 pages.
Japanese Office Action, Application No. 2017-545245, dated Oct. 30, 2018, 11 pages.
Japanese Office Action, Application No. 2017-545230, dated Nov. 6, 2018, 10 pages.
Application and File History for U.S. Appl. No. 15/521,082, filed Apr. 21, 2017, Inventor Aoun.
Application and File History for U.S. Appl. No. 15/553,785, filed Aug. 25, 2017, Inventor Hepworth.
Communication pursuant to Article 94(3) EPC for Application No. 15793718.6, dated Dec. 20, 2018, 5 pages.
European Search Report for Application No. EP18190846 dated Dec. 21, 2018, 10 pages.
European Search Report for European Application No. EP21166365.3, dated Jul. 21, 2021, 12 pages.
Examination Report for European Application No. 15725399.8, dated Jun. 4, 2019, 5 pages.
International Preliminary Report on Patentability for Application No. PCT/EP2015/074395, dated May 4, 2017, 7 pages.
International Preliminary Report on Patentability for Application No. PCT/EP2016/073472, dated Apr. 3, 2018, 9 pages.
International Search Report for Application No. PCT/EP2016/073472, dated Jan. 31, 2017, 3 pages.
International Search Report for Application No. PCT/GB2015/051253, dated Nov. 16, 2015, 6 pages.
International Written Opinion for Application No. PCT/EP2016/054159, dated Jun. 9, 2016, 7 pages.
International Written Opinion for Application No. PCT/EP2016/054232, dated Aug. 24, 2016, 8 pages.
Merriam-Webster Dictionary, Definition of "throughout," the Free Merriam-Webster Dictionary, Mar. 7, 2015, http://www.merriam-webster.com/dictionary/throughout, 15 pages.
Notice of Reasons for Refusal for Japanese Application No. 2018-152380, dated Jun. 30, 2020, 22 pages.
Office Action dated Aug. 24, 2020 for Chinese Application No. 201680056939.7, 33 pages.
Office Action dated Jun. 2, 2020 for Japanese Application No. 2017-545230, 5 pages.
Office Action dated May 15, 2018 for Japanese Application No. 2017-522122, 29 pages.
Office Action dated Jul. 2, 2018 for Chinese Application No. 201580023549.5, 23 pages.
Office Action dated Jul. 30, 2019 for Japanese Application No. 2017-545230, 12 pages.
Office Action dated Oct. 30, 2018 for Korean Application No. 1020177013874, 19 pages.
Office Action dated May 7, 2019 for Japanese Application No. 2018-515290, 8 pages.
Search Report For Russian Application No. 2018106929, dated Aug. 20, 2021, 2 pages.
Search Report dated Apr. 23, 2015 for Great Britain Application No. 1418817.1, 5 pages.
Written Opinion for Application No. PCT/EP2015/074395, dated Feb. 1, 2016, 5 pages.
Written Opinion for Application No. PCT/EP2016/073472, dated Jan. 31, 2017, 8 pages.
Written Opinion for Application No. PCT/GB2015/051253, dated Nov. 16, 2015, 7 pages.
First Examination Report dated Dec. 11, 2019 for New Zealand Application No. 752875, 4 pages.
International Preliminary Report on Patentability for Application No. PCT/EP2017/077633, dated May 16, 2019, 7 pages.
International Search Report and Written Opinion for Application No. PCT/EP2017/077633, dated Feb. 5, 2018, 8 pages.
Office Action for Canadian Application No. 3,042,128, dated Aug. 11, 2020, 6 pages.
Office Action for Chinese Application No. 201780067522.5, dated Jan. 8, 2021, 18 pages.
Office Action for Chinese Application No. 201780067522.5, dated Jan. 10, 2022, 6 pages.
Office Action for Japanese Application No. 2019-522376, dated Sep. 1, 2020, 9 pages.
Office Action dated Dec. 5, 2019 for Russian Application No. 2019116869, 13 pages.
Search Report dated Aug. 20, 2020 for Japanese Application No. 2019-522376, 36 pages.
Anonymous: "iFUSE—the Heat not Burnhybrid—Heat Not Burn" (https://heatnotburn.co.uk/ifuse-heat-not-burn-hybrid/), Jan. 4, 2018, 15 pages.
International Search Report and Written Opinion for International Application No. PCT/EP2019/070009, dated Nov. 6, 2019, 17 pages.

(56) References Cited

OTHER PUBLICATIONS

International Search Report and Written Opinion for International Application No. PCT/EP2019/070017, dated Dec. 2, 2019, 13 pages.
Notice of Reasons for Refusal for Japanese Application No. 2021-505274 dated Apr. 12, 2022, 9 pages.
Office Action For Russian Application No. 2021104828, dated Aug. 18, 2021, 17 pages.
"International Preliminary Report on Patentability for Application No. PCT/GB2015/051253, dated Nov. 10, 2016", 9 pages.
"International Preliminary Report on Patentability received for PCT Patent Application No. PCT/EP2019/070009, dated Feb. 11, 2021", 10 pages.
"International Preliminary Report on Patentability received for PCT Patent Application No. PCT/EP2019/070017, dated Feb. 11, 2021", 8 pages.
"Reasons of Rejection received for Korean Patent Application No. 10-2021-7005666, dated Feb. 27, 2023", 7 pages (English Translation Only).

\* cited by examiner

APPARATUS FOR GENERATING AN INHALABLE MEDIUM

CROSS-REFERENCE TO RELATED APPLICATIONS

The present application is a National Phase entry of PCT Application No. PCT/EP2016/054232, filed Feb. 29, 2016, which claims priority from GB Patent Application No. 1503411.9, filed Feb. 27, 2015, and GB Patent Application No. 1517470.9, filed Oct. 2, 2015 each of which is hereby fully incorporated herein by reference.

TECHNICAL FIELD

The present disclosure relates to an apparatus and methods for generating an inhalable medium.

BACKGROUND

Smoking articles such as cigarettes, cigars and the like burn tobacco during use to create tobacco smoke. Attempts have been made to provide alternatives to these articles that burn tobacco by creating products that release compounds without burning.

Examples of such products are heating devices which release compounds by heating, but not burning, the material. The material may be for example tobacco or other non-tobacco products, which may or may not contain nicotine. As another example, there are so-called e-cigarette devices. These devices typically contain a liquid which is heated to vaporize the liquid to produce an inhalable vapor or aerosol. The liquid may contain nicotine and/or flavorings and/or aerosol-generating substances, such as glycerol. The known e-cigarette devices typically do not contain or use tobacco.

SUMMARY

According to a first aspect of the present disclosure, there is provided an apparatus for generating an inhalable medium, the apparatus comprising: a liquid container for holding a liquid; a heater for volatilizing liquid held in the container; and a receiving portion for receiving a plurality of discrete material elements; the apparatus being arranged such that in use liquid volatized by the heater passes, in the form of at least one of a vapor and an aerosol, through one or more of the plurality of discrete material elements received by the receiving portion in use thereby to entrain one or more constituents of the one or more of the plurality of discrete material elements to produce the inhalable medium.

The container and the receiving portion may form an integral unit.

The receiving portion may be connectable to, and removable from, the liquid container.

The apparatus may be arranged such that the liquid volatized by the heater passes, in the form of at least one of a vapor and an aerosol, sequentially through each of the plurality of discrete material elements received by the receiving portion in use.

The apparatus may be arranged such that the liquid volatized by the heater passes, in the form of at least one of a vapor and an aerosol, simultaneously through each of the plurality of discrete material elements received by the receiving portion in use.

The apparatus may be arranged such that the liquid volatized by the heater flowing in the form of at least one of a vapor and an aerosol flows in a plurality of discrete streams, each stream for passing through a respective one of the plurality of discrete material elements received by the receiving portion in use.

The apparatus may be arranged to allow independent control of a flow of each discrete stream.

The independent control may comprise control to stop the flow of the vapor or aerosol through one or more of said plurality of discrete material elements whilst allowing the flow of the vapor or aerosol through one or more others of the plurality of discrete material elements.

The apparatus may comprise one or more retainers for retaining the plurality of material elements received by the receiving portion in use, wherein the one or more retainers are arranged so as to allow vapor or aerosol to pass there through.

The receiving portion may be arranged to allow user access to one or more of the plurality of discrete material elements received by the receiving portion in use.

The receiving portion may be arranged to allow one or more of: changing an order of one or more of the plurality of discrete material elements received by the receiving portion in use; adding one or more of the discrete material elements to the receiving portion; removing one or more of the discrete material elements from the receiving portion; and exchanging one or more of the plurality of discrete material elements received by the receiving portion in use for one or more other of the discrete material elements.

The receiving portion may have received therein a said plurality of discrete material elements.

The plurality of discrete material elements may be in an ordered arrangement.

Each of the plurality of discrete material elements may be the same.

One of the plurality of discrete material elements may have a property different to that of another of the plurality of discrete material elements.

Each one of the plurality of discrete material elements may have a property different to that of each other one of the plurality of discrete material elements.

The property may be one of aroma or flavor.

The plurality of discrete material elements may be stacked one on top of the other.

One or more of the plurality of discrete material elements may comprise material in solid form.

One or more of the plurality of discrete material elements may be a material in solid form, and the receiving portion may be a receptacle for receiving material in solid form.

A dimension of each of the plurality of discrete material elements relative to a dimension of the receptacle may be such that in use an ordered arrangement of the plurality of discrete material elements remains fixed.

The receptacle may comprise an inner portion and an outer portion, and the material in solid form may be annular in shape so as to be received between the inner portion and the outer portion.

Liquid volatized by the heater may pass, in the form of at least one of a vapor and an aerosol, from one of the inner portion and the outer portion, through the material in solid form, to the other one of the inner portion and the outer portion.

Each of the plurality of discrete material elements may be separated from one another by an impermeable membrane.

One or more of the discrete material elements may comprise: a material container for containing material; and material contained within the material container.

The material container may comprise a connector, and the receiving portion is for receiving the connector of the material container.

The material container may comprise a connector allowing connection of the material container to another such material container.

The material container may be annular in shape.

The material contained within the material container may be material in solid form.

The material in solid form may be or may comprise tobacco.

The material in solid form may be or may comprise a flavored solid material.

According to a second aspect of the present disclosure, there is provided a method of generating an inhalable medium using an apparatus comprising a container holding a liquid, a heater for volatizing the liquid, a plurality of discrete material elements, the method comprising: volatizing the liquid held in the container; and passing at least one of a vapor and an aerosol formed by the volatized liquid through one or more of said plurality of discrete material elements thereby to entrain one or more constituents of the one or more of said plurality of discrete material elements to produce the inhalable medium.

According to a third aspect of the present disclosure, there is provided a cartridge for use with an apparatus for generating an inhalable medium, the cartridge comprising: a container for holding a liquid; and a receiving portion for receiving a plurality of discrete material elements; the cartridge being arranged such that in use liquid exiting the container can flow, in the form of at least one of a vapor and an aerosol, through one or more of the plurality of discrete material elements received by the receiving portion in use, thereby to entrain one or more constituents of the one or more of the plurality of discrete material elements to produce the inhalable medium.

According to a fourth aspect of the present disclosure, there is provided a receptacle for receiving a plurality of discrete material elements, the receptacle being for use with an apparatus for generating an inhalable medium, the apparatus comprising a container for holding a liquid, the receptacle being arranged such that in use liquid exiting the container flowing in the form of at least one of a vapor and an aerosol can flow through one or more of the plurality of discrete material elements received by the receptacle in use, thereby to entrain one or more constituents of the one or more of the plurality of discrete material elements to produce the inhalable medium.

According to a fifth aspect of the present disclosure, there is provided a cap for use with an apparatus for generating an inhalable medium flowing in the form of one of a vapor and an aerosol, the cap comprising: a connecting portion for forming a seal between a mouthpiece of the apparatus and the cap; and a receiving portion for receiving material; the cap being arranged such that in use, the inhalable medium, flowing in the form of one of a vapor and an aerosol, can flow from the mouthpiece into the cap and through the material received by the receptacle, thereby to entrain one or more constituents of the material to produce the inhalable medium, into a mouth of a user.

The connecting portion may be shaped so as to allow the connecting portion to form a seal between the cap and any one of a plurality of different shaped or dimensioned mouthpieces.

The seal may be an air tight seal.

The connecting portion may be arranged such that the cap is removably connectable to the mouthpiece.

The connecting portion may comprise a tapered recess.

The recess may be tapered such that a diameter of the recess decreases from an open end of the recess to a closed end of the recess.

The recess may be a frustroconical recess.

The connecting portion may be or may comprise rubber.

The cap may be shaped so as to allow the connecting portion to form a seal between the cap and a further such cap.

The receiving portion may have material received therein.

The material may be material in solid form.

The solid material may be or may comprise tobacco.

The solid material may be or may comprise a solid flavored material.

BRIEF DESCRIPTION OF THE DRAWINGS

Further features and advantages will become apparent from the following description of embodiments of the disclosure, given by way of example only, which is made with reference to the accompanying drawings, in which.

DETAILED DESCRIPTION

Figure 1:
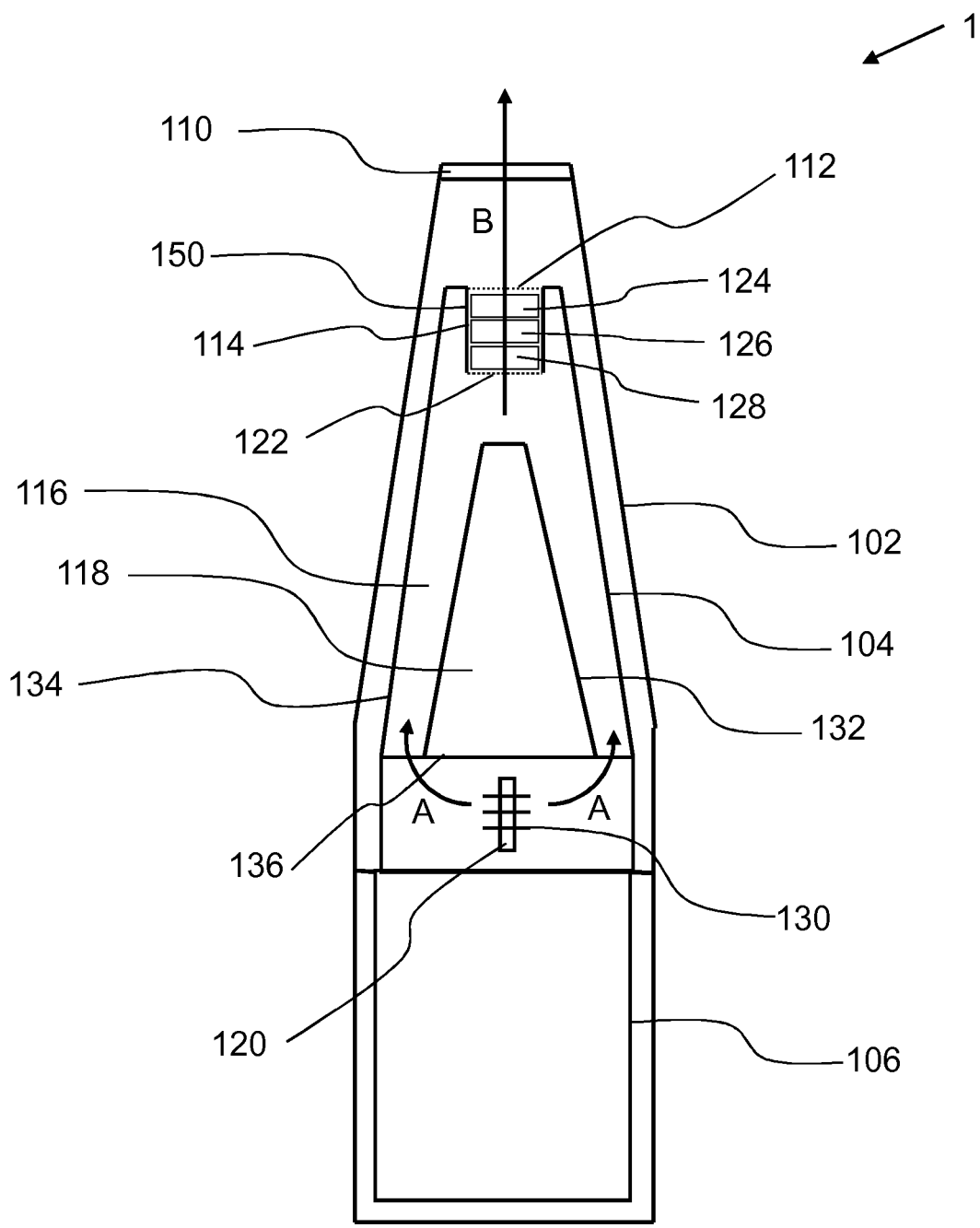
FIG. 1 shows a schematic cross section of an exemplary apparatus containing an exemplary cartridge.

Referring to FIG. 1, a schematic cross-section of an example of an apparatus 1 for generating an inhalable medium is illustrated. In broad outline, the apparatus 1 volatilizes a liquid to form a vapor or an aerosol which passes through a plurality of discrete solid material elements so as to produce an inhalable medium that contains one or more constituents derived from the material.

In this respect, first it may be noted that, in general, a vapor is a substance in the gas phase at a temperature lower than its critical temperature, which means that for example the vapor can be condensed to a liquid by increasing its pressure without reducing the temperature. On the other hand, in general, an aerosol is a colloid of fine solid particles or liquid droplets, in air or another gas. A "colloid" is a substance in which microscopically dispersed insoluble particles are suspended throughout another substance.

Returning to FIG. 1, the apparatus 1 comprises an outer body 102 which houses a cartridge 104 and a battery 106, and a mouthpiece 110 on which a user can draw. The cartridge 104 is connected to, but removable from, the battery 106. At least a portion of the outer body 102 may be removed so as to expose the cartridge 104, and hence allow installation, removal and/or replacement of the cartridge 104. The cartridge 104 has a liquid container 132 for containing liquid 118 and a receiving portion 150 comprising a receptacle 114 for receiving a plurality of discrete solid material elements 124, 126, 128 (also referred to herein as material elements).

As described in more detail below, the material elements 124, 126, 128 may be, for example, self-supporting disks 124, 126, 128 of solid material permeable to aerosol or vapor, or comprise solid material packaged in a self-supporting container (not shown) that itself is permeable to aerosol or vapor. The solid material (also referred to herein as material in solid form) may be for example tobacco, or other flavored materials that may be used to create a desired taste or aroma, or have other properties, such as nicotine content. In one example, each material element 124, 126, 128 may comprise a solid material with a flavor, aroma, or other properties that are the same as the solid material of the other ones of the plurality of material elements 124, 126, 128. For example, each of the plurality of material elements 124, 126, 128 may be the same. In this example, by controlling the number of material elements 124, 126, 128 that the vapor or aerosol passes through, a user can control the amplitude of the flavor or other properties of the solid material imparted to the inhalable medium produced by apparatus 1. In another example, each material element 124, 126, 128 may comprise a solid material with a flavor, aroma, or other properties that are different from the solid material of other ones of the plurality of material elements 124, 126, 128. For example, one of the plurality of material elements 124, 126, 128 may have a property (e.g. aroma, flavor, etc.) different to that of another of the plurality of material elements 124, 126, 128, and/or each one of the plurality of material elements 124, 126, 128 may have a property different to that of each other one of the plurality of material elements 124, 126, 128. In this example, the material elements 124, 126, 128 may therefore be combined in different ways to allow a user to customize the properties (e.g. flavor) of the inhalable medium produced by the apparatus 1. In other examples, any combination of material elements 124, 126, 128 may be used, for example to customize the amplitude of any one or any combination of flavors or other properties of the plurality of material elements 124, 126, 128.

In the example of FIG. 1, the receptacle 114 is integral to the cartridge 104. The receptacle 114 comprises a first retainer 122 and a second retainer 112 to retain the plurality of material elements 124, 126, 128 within the receptacle 114. The plurality of material elements 124, 126, 128 may be received in receptacle 114 in an ordered arrangement. For example, the plurality of material elements 124, 126, 128 may be manually inserted into the receptacle 114 in an ordered positional arrangement. The dimensions of the material elements 124, 126, 128 relative to the receptacle 114 may be such that, once inserted, the ordered positional arrangement of the material elements 124, 126, 128 may remain fixed unless a manual reordering of one or more of the material elements 124, 126, 128 is performed. In the example of FIG. 1, the plurality of material elements 124, 126, 128 are stacked one on top of the other, i.e. a second material element 126 is stacked on top of a first material element 128, and a third material element 124 is stacked on top of the second material element. Although in the example of FIG. 1 there are three material elements 124, 126, 128, it will be appreciated that in some examples there may only be two material elements, and in other examples there may be N material elements, where N is any positive integer greater than or equal to 2. The first and second retainers 112, 122 are permeable so as to allow gas phase material, such as vapor or an aerosol, to pass through, but to prevent material in the solid phase, such as material elements 128, 126, 124, from passing through. For example, the first and second retainers 112, 122 may comprise a mesh made from metal or plastic or ceramic or rubber or the like, or a permeable membrane, or simply a disc with holes running there through. The retainers 112, 122 may be integral to the receptacle 114, and hence may be integral to the cartridge itself.

In this example, the cartridge 104 is arranged so that as the liquid 118 is volatilized so as to produce an aerosol of liquid droplets or sufficiently heated to produce a vapor, at least some and, in some embodiments, all or substantially all of the aerosol or vapor passes through each of the plurality of material elements 124, 126, 128 sequentially, for example so as to pick up flavor from each material element 124, 126, 128.

In this example, the liquid container 132 is provided generally centrally of the cartridge 104. The liquid container 132 in the example shown is frustoconical in shape, but may have a different shape, such as conical, cylindrical, etc. The liquid container 132 is surrounded by an outer shell 134 which defines an annular channel 116 around the outside of the length of the liquid container 132 and which extends from one end of the liquid container 132 to the other. The liquid container 132 may be formed of rigid, watertight and airtight materials, such as metal, suitable plastics, etc.

The cartridge 104 is provided with a heater 130 and a wick 120 in (thermal) contact with the heater 130. In this example, the heater 130 and the wick 120 are provided as a single unit. In this case, where the cartridge 104 includes a heater 130, such a cartridge is often referred to as a "cartomizer." The orientation of the heater 130 is shown schematically and, for example, the heater 130 may be a coil having its longitudinal axis perpendicular to the longitudinal axis of the cartridge 104 rather than parallel as shown in FIG. 1. The wick 120 is in contact with the liquid 118. This may be achieved by, for example, the wick 120 being inserted through a through hole (not shown) in an end wall 136 of the liquid container 132. Alternatively or additionally, the end wall 136 may be a porous member which allows liquid to pass through from the liquid container 132, and the wick 120 may be in contact with the porous end wall 136. The end wall 136 may be for example in the form of a porous ceramic disk. A porous end wall 136 of this type helps to regulate the flow of liquid onto the wick 120. The wick 120 is generally absorbent and acts to draw in liquid 118 from the liquid container 132 by capillary action. The wick 120 can be non-woven and may be for example a cotton or wool material or the like, or a synthetic material, including for example polyester, nylon, viscose, polypropylene or the like, or a ceramic material.

In this example, the cartridge 104 is connected to the battery 106 to enable the heater 130 to be powered. When the heater 130 is powered (which may be instigated for example by the user operating a button of the apparatus 1 or by a puff detector of the overall apparatus, as is known per se), liquid 118 drawn in from the liquid container 132 by the wick 120 is heated by the heater 130 to volatilize or vaporize the liquid. As the user draws on the mouthpiece 110, air is drawn through an air inlet (not shown). The liquid 118 is volatized or vaporized by the heater 130 into air from the air inlet (not shown) thereby to produce one of a vapor and an aerosol. The vapor or aerosol passes into the annular channel 116 around the outside of the length of the liquid container 132 as shown by arrows A. The vapor or aerosol is drawn towards the first retainer 122 of the receptacle 114, and sequentially through the plurality of material elements 124, 126, 128, as shown by arrow B. The vapor or aerosol picks up flavor (and/or other constituents) from each of the material elements 124, 126, 128. In the case that the solid material of any one of the material elements 124, 126, 128 contains or includes nicotine, the vapor or aerosol may also contain nicotine entrained from that solid material. The vapor or aerosol can then exit through the second retainer 124 of the cartridge 104 and out through the mouthpiece 110 (as shown by arrow B). A one way valve (not shown) may be provided at or near either one of the first or second retainers 122, 124, or at or near the mouthpiece 110 so that the vapor or aerosol can only exit the cartridge 104 and cannot back-flow to the heater 130 or the electronics (not shown) of the apparatus 1.

The material elements 124, 126, 128 may be removable from the receptacle 114. For example, the second retainer 112 may be removable so as to allow access to the material elements 124, 126, 128. As another example, a portion of the cartridge 104 itself, for example a door or hatch like portion (not shown), may be removable so as to allow access to one or more of the material elements 124, 126, 128. In such a way, a user may add, remove, or exchange one or more material elements 124, 126, 128 in the receptacle 114. The material elements 124, 126, 128 may be manually inserted in the receptacle 114 in an ordered positional arrangement. A user may change the order of two or more of the plurality of material elements 124, 126, 128. Optionally, the first retainer 112 (i.e. the upper retainer as drawn in FIG. 1) may be omitted such that the plurality of material elements 124, 126, 128 are held in the receptacle 114 by only the second retainer 122 (i.e. the lower retainer as drawn in FIG. 1) and, for example, gravity. Alternatively, the mouthpiece 110 or other component of the outer body 102 of apparatus 1 may be arranged so as to prevent the plurality of material elements 124, 126, 128 from falling out of receptacle when assembled, but allow the user access to the material elements 124, 126, 128 when the mouthpiece of portion of the outer body is removed. This allows a user easy access to the plurality of material elements. In other examples, the material elements 124, 126, 128 may not be removable from the receptacle 114, and the cartridge 104 is disposable.

In the above example described with reference to FIG. 1, the receptacle 114 was integral to the cartridge 104. However, this need not necessarily be the case. In other examples, the receptacle 114 is connectable to, and removable from, the cartridge 104.

Figure 2:
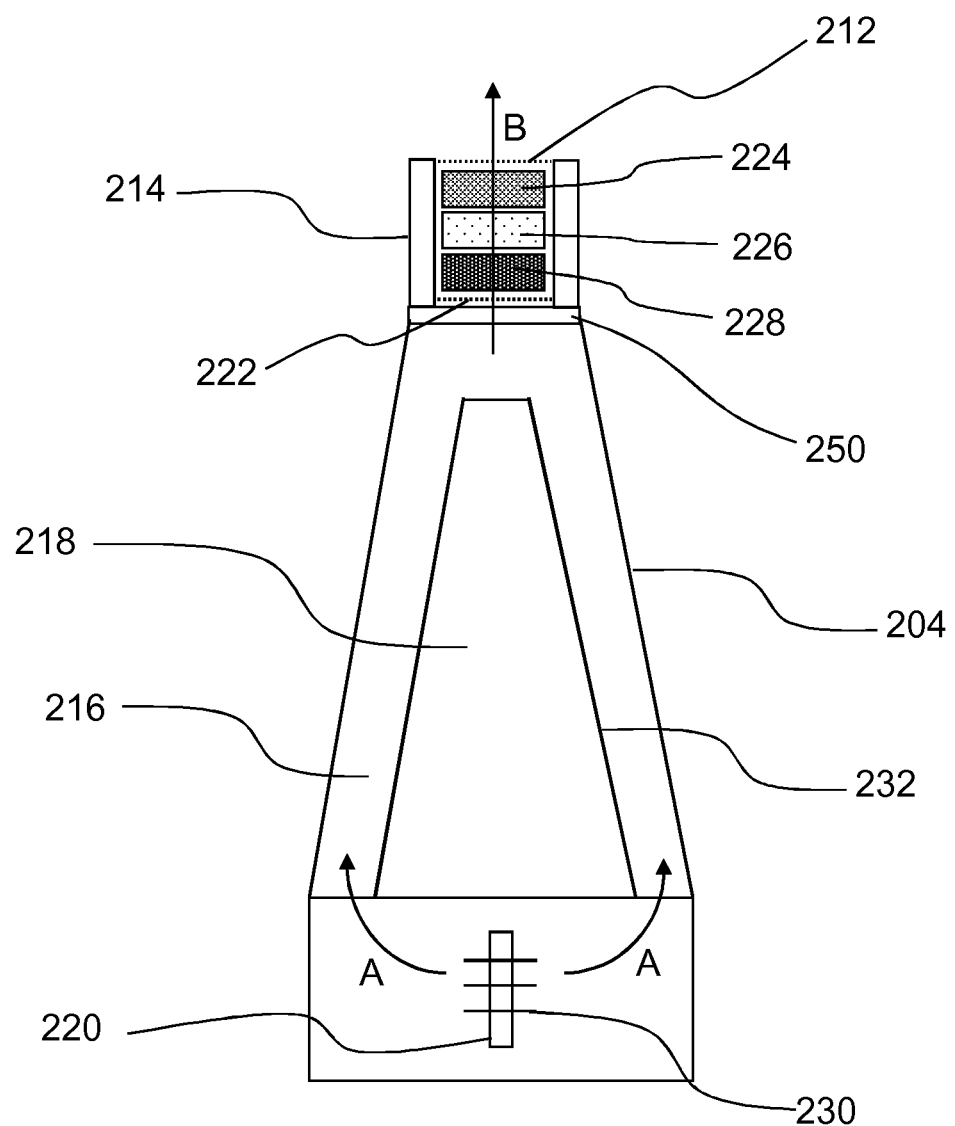
FIG. 2 shows a schematic cross-section of an exemplary cartridge.

FIG. 2 illustrates a schematic cross section of an example cartridge 204 that may be used, for example, with apparatus 1 shown in FIG. 1, for example, in place of the cartridge 104 of FIG. 1. In the cartridge 204 shown in FIG. 2, a receptacle 214 is connectable to, and removable from, a receiving portion 250 of the cartridge 204. For brevity, features in FIG. 2 that do not differ from those features already described with reference to FIG. 1 will not be described in detail again.

Referring now to the example of FIG. 2, a cartridge 204 comprises a receiving portion 250 which allows a receptacle 214 to be removably connected to the cartridge 204. In this example, the receiving portion 250 is at an end of the cartridge opposite to the end comprising the heater. In this example, the receptacle 214 is annular in shape, and has received therein a plurality of material elements 224, 226, 228. The plurality of material elements 224, 226, 228 are stacked one on top of the other, i.e. a second material element 226 is stacked on top of a first material element 228, and a third material element 224 is stacked on top of the second material element 226. The receptacle 214 comprises first retainer 222 and second retainer 212 for retaining the material elements 224, 226, 228 within the receptacle. The retainers 222, 212 allow vapor and aerosol to pass through them, but do not allow the material elements 224, 226, 228 to pass through them. In this example, the receptacle 214 is placed in, and removably connected to, the receiving portion 250 of the cartridge 204. For example, the receiving portion 250 may comprise a thread (not shown) allowing a reciprocal thread (not shown) of the receptacle 114 to engage therewith. In other examples, a push fit or a snap fit or the like may be used between the receiving portion 250 and the receptacle 214.

One or both of the retainers 222, 212 may be removable from the receptacle 214 so as to allow access to one or more of the plurality of material elements 224, 226, 228, and hence to allow a user to add, remove, exchange one or more, or change the order of, of the material elements 224, 226, 228, in the receptacle. In other examples, the retainers 222, 212 are not removable, and the receptacle 214 is disposable. The user may replace the entire receptacle 214.

In this example, briefly, liquid 218 drawn in from a liquid container 232 by a wick 220 is heated by a heater 230 to volatilize or vaporize the liquid. As the user draws on a mouthpiece (not shown in FIG. 2), air is drawn through an air inlet (not shown) and the liquid 218 is volatized or vaporized by the heater 230 into the air to produce one of a vapor and an aerosol. The vapor or aerosol passes into an annular channel 216 around the outside of the length of the liquid container 232 as shown by arrows A in FIG. 2. The vapor or aerosol is drawn towards and through the receiving portion 250, through the first retainer 222 of the receptacle 214, and sequentially through the plurality of material elements 224, 226, 228, as shown by arrow B in FIG. 2. The vapor or aerosol picks up flavor (and/or other constituents) from each of the material elements 224, 226, 228. The vapor or aerosol then exits through the second retainer 224 of the cartridge 104 (as shown by arrow B) for inhalation by the user.

In the above examples described with reference to FIGS. 1 and 2, the plurality of material elements 124, 126, 128, etc., were received in a common receptacle 114, 214, and were held in place by one or more retainers 122, 112. However, this need not necessarily be the case. In other examples, each of the plurality of material elements 124, 126, 128 etc. are removably connectable to a receiving portion 250, etc., of a cartridge 104 etc., and to each other.

Figure 3:
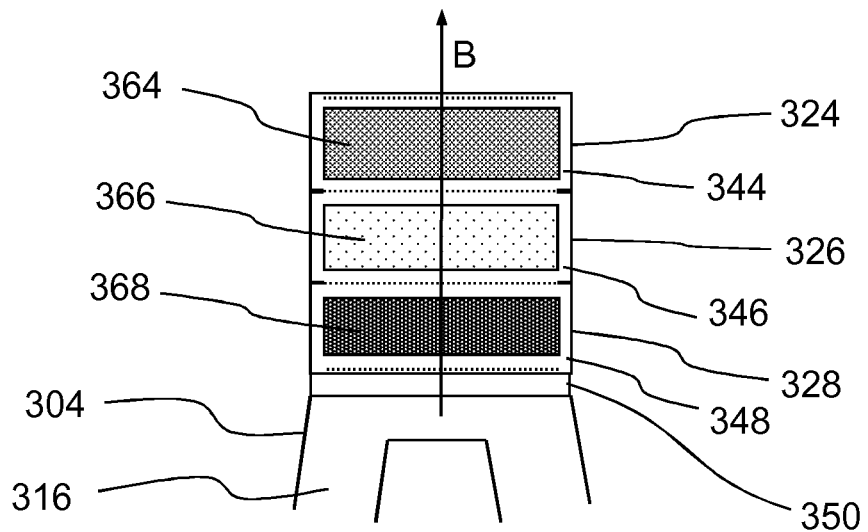
FIG. 3 shows a schematic cross-section of some exemplary containers.
Figure 4:
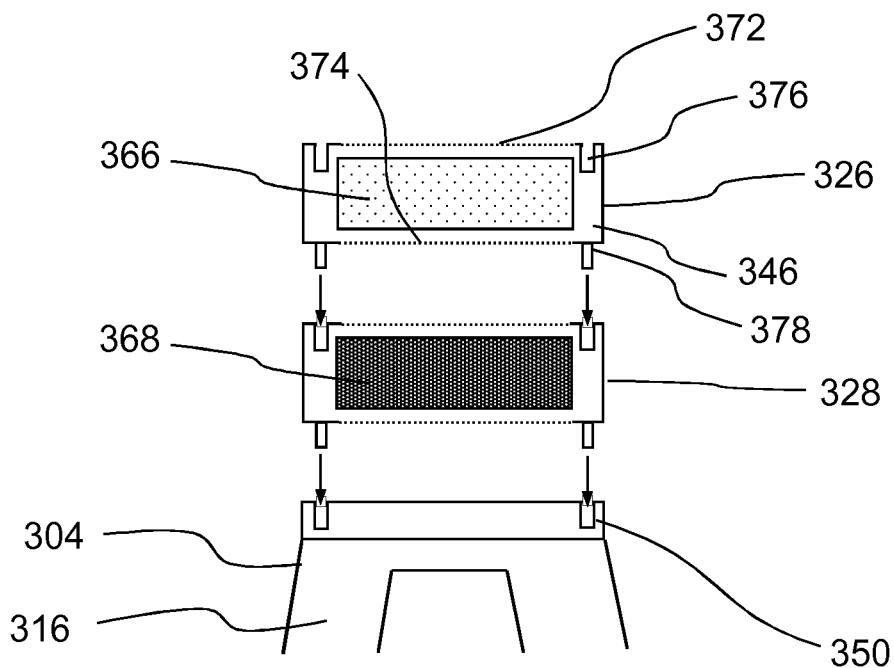
FIG. 4 shows a schematic cross-section of some exemplary containers.

FIGS. 3 and 4 illustrate a schematic cross section of an example plurality of material elements 324, 326, 328 that are removably connectable to a receiving portion 350 of a cartridge 304. The cartridge 304 may, for example, be used in apparatus 1, for example, instead of the cartridge 104 shown in FIG. 1. For brevity, features that do not differ from those already described with reference to FIGS. 1 and 2 are not shown in FIGS. 3 and 4 and will not be described again.

Referring to FIGS. 3 and 4, a cartridge 304 comprises a receiving portion 350 for receiving one of a plurality of material elements 324, 326, 328. In this example, each of the material elements 324, 326, 328 comprises a self-supporting container 344, 346, 348 (respectively) that contains a solid material 364, 366, 368 (respectively). As best seen in FIG. 4, with reference to material element 326, each container 346 comprises a first retainer 374 and a second retainer 372 for retaining the solid material 366 in the container 346. The first and second retainers 374, 372 allow vapor or aerosol to flow there through, but do not allow solid material 366 to pass there through. Each material element 326 comprises a connector 378 for connecting the material element 326 to another material element. The connector 378 additionally allows each material element 326 to be connected to the receiving portion 350 of the cartridge 304. The connectors 378 allow for the plurality of material elements 324, 326, 328 to be received in the receiving portion 350 in an ordered arrangement. The connectors 378 may be such that, once connected, the ordered position arrangement of the plurality of material elements 324, 326, 328 may remain fixed unless a manual reordering of one or more of the material elements 124, 126, 128 is performed. In the example shown in FIG. 4, each material element 326 comprises a male connection portion 378 and a corresponding female connection portion 376 on the opposite side of the material element to the male connection portion 378 to allow the material elements to be stacked. The receiving portion 350 may also comprise such a connecting portion 378, 376 to allow a material element 324, 326, 328 to be connected thereto. The connecting portions 378 and 376 may be any suitable connecting portions, for example reciprocal threads, reciprocal elements of a push fit or a snap fit or the like.

In this example, a male connecting portion 378 of a first material element 328 is inserted into a female connecting portion 376 of the receiving portion 350 of the cartridge 304 so as to connect (i.e. fluidically and mechanically connect) the first material element 328 to the receiving portion 350 and hence the cartridge 304. The male connecting portion 378 of a second material element 326 is then inserted into the female connecting portion 376 of the first material element 328 so as to connect (i.e. fluidically and mechanically connect) the second material element 326 to the first material element 328, and hence, via receiving portion 350, to the cartridge 304. Similarly, material element 324 may be connected to material element 326. Similarly to as described above, when a user draws on a mouthpiece (not shown) therefore, vapor or an aerosol flows sequentially through each of the solid materials 364, 366, 368 contained in material elements 324, 326, 328 (respectively). Since the plurality of material elements 324, 326, 328 can be interchangeably stacked, a user can easily customize the flavor and/or other properties of the inhalable medium emanating therefrom.

In the above examples described above with reference to FIGS. 1-4, the vapor or aerosol flowed sequentially through the plurality of material elements 124, 126, 128 etc. However, this need not necessarily be the case. In other examples, the aerosol or vapor drawn from a cartridge 104 etc. flows through each material element 124, 126, 128, etc., simultaneously.

Figure 5:
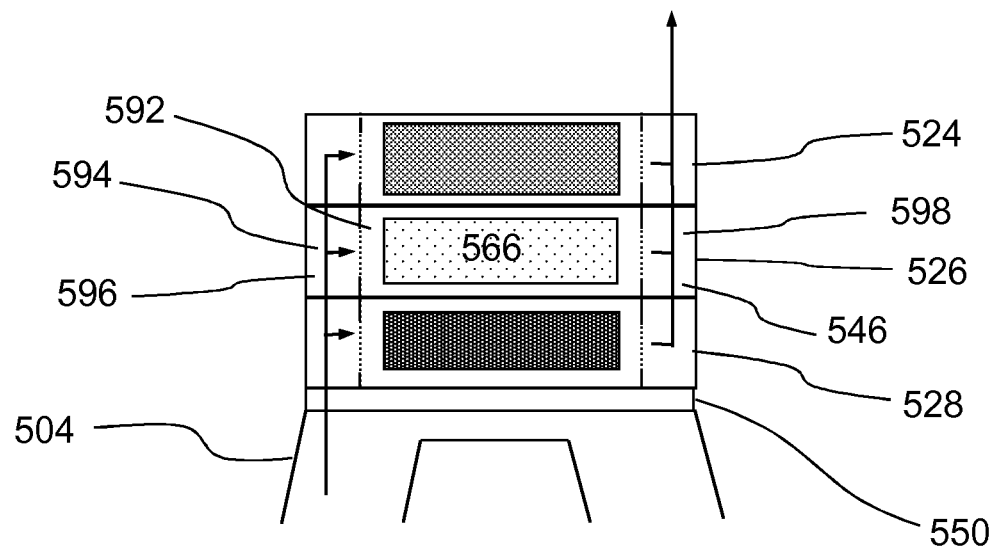
FIG. 5 shows a schematic cross-section of some exemplary containers.

FIG. 5 illustrates a schematic cross section of an example plurality of material elements 524, 526, 528 in which the aerosol or vapor drawn from a cartridge 504 flows through each material element simultaneously. The cartridge 504 may, for example, be used in apparatus 1 shown in FIG. 1, for example, in place of the cartridge 104 shown in FIG. 1. For brevity, features that do not differ from those features already described with reference to FIGS. 1-4 are not shown in FIG. 5 and will not be described again.

Referring to FIG. 5, a plurality of material elements 524, 526, 528 are connected together and are received in and connected to a receiving portion 550 of a cartridge 504. Each of the material elements 524, 526, 528 are basically the same, except that they contain different solid materials (e.g. solid materials with different properties such as aroma, flavor etc.), although of course it will be appreciated that this need not necessarily be the case and instead, for example, two or more of the material elements 524, 526, 528 may contain the same solid material (e.g. solid materials with the same or similar properties such as aroma, flavor, etc.). For brevity, only the characteristics of material element 526 will be described. Material element 526 comprises a self-supporting container 546 that contains solid material 566 in a central cavity 592. The container 546 also comprises an outer cavity 594 that surrounds the central cavity 592. For example, the outer cavity 594 may be annular. The outer cavity 594 is divided into two portions 596, 598 such that vapor or aerosol in a first portion 596 of the outer cavity 594 must flow through the central cavity 594, and hence solid material 566, in order to reach the second portion 598 of the annular cavity 594.

The material elements 524, 526, 528 are arranged such that vapor or aerosol in the first portion 596 of a first material element 528 may flow into the first portion 596 of a second material element 526 to which the first material element 528 is connected, but not the second portion 598 of the second material element 528. Similarly, the material elements 524, 526, 528 are arranged such that vapor or aerosol in the second portion 598 of a first material element 528 may flow into the second portion 598 of a second material element 526 to which the first material element 528 is connected, but not the first portion 596 of the second material element 528.

Similarly, for a material element 528 adjacent and connected to the receiving portion 550 of the cartridge 504, the material element 528 is arranged such that vapor or aerosol from the cartridge 504 may only flow into the first portion 596 of the outer cavity 594 of the material element 528, but not the second portion 598. Similarly, for a material element 524 that is the furthest of the plurality of material elements 524, 526, 528 from the receiving portion 550 of the cartridge 504, vapor or aerosol may flow out of the second portion 598 of the outer cavity 594 for inhalation by a user, but not out of the first portion 596.

As shown by the arrows in FIG. 5, according to the above described arrangement, vapor or aerosol may be drawn from the cartridge 504, split into a plurality of individual streams that flow simultaneously through a respective material element 524, 526, 528, before being recombined and exiting the material elements for inhalation by a user.

Figure 6:
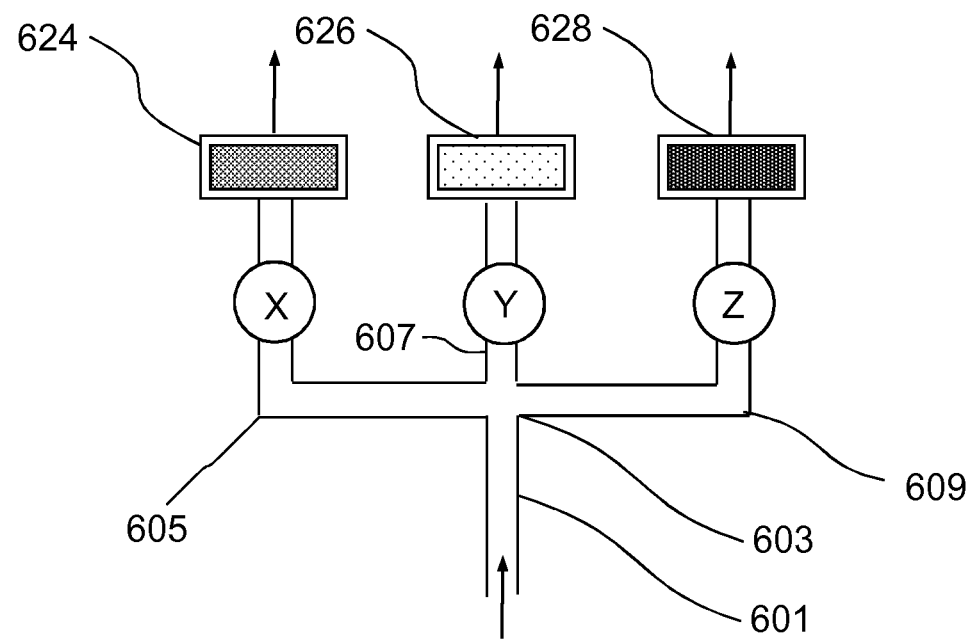
FIG. 6 shows a schematic flow path through some exemplary containers.

In some examples, the relative flow of the vapor or aerosol through each of the plurality of material elements 124, 126, 128, etc., may be controlled. FIG. 6 illustrates schematically a flow path 601 in which vapor or aerosol may be controlled to flow at different rates through each different material element 624, 626, 628. The flow path 601 comprises a branch 603 upstream of the material elements 624, 626, 628 that splits the vapor or aerosol flow into a plurality of discrete streams 605, 607, 609 each associated with each material element 624, 626, 628 (respectively). Each discrete stream 605, 607, 609 has a regulator X, Y, Z (respectively) that can regulate the flow of vapor or aerosol into the respective material element 624, 626, 628. The regulators X,Y,Z can be independently controlled. For example, each regulator X,Y,Z may be adjustable by the user mechanically, for example via an adjustment lever (not shown) accessible to the user. The regulators X,Y,Z may be adjustable electronically, for example, by a user pressing one or more buttons, or interacting with an user interface, located on the outside of the overall apparatus (not shown). Alternatively or additionally, the user may control the regulators X,Y, Z via controls or an interface external to the overall apparatus (not shown), for example via radio control signals, or Bluetooth or the like from a separate control device, such as a smartphone or the like. The regulators X,Y,Z may take the form of a valve. As another example, the regulators X,Y,Z may each comprise a plurality of overlapping perforated plates, wherein as the plates move relative to each other, the perforations in the plates align or misalign so as to allow an increased or decreased flow through the plates accordingly. Being able to regulate the flow of vapor or aerosol through each one of the material elements 624, 626, 628 independently allows a user to further customize the properties (e.g. flavor) of the inhalable medium produced by an apparatus 1.

In some examples, independent control of the streams comprises control to stop the flow of the vapor or aerosol through one or more of the material elements 624, 626, 628 whilst allowing the flow of the vapor or aerosol through one or more others of the material elements 624, 626, 628. For example, the user may control the regulators X,Y,Z such that vapor or aerosol only flows through, say, one of the material elements (say, 624) and not through the other material elements 626, 628 etc. In such a way, a user may control the apparatus 1 such that, even though a plurality of material elements 624, 626, 628 are available, the vapor or aerosol only passes through one material element (say 624) at a time. The user may control the apparatus 1 so as to select on each puff (i.e. inhalation) which of the plurality of the material elements 624, 626, 628 the vapor or aerosol is to pass through and so may vary their taste experience from puff to puff.

There may also be a bypass channel (not shown in the figures) that bypasses all of the plurality of material elements, and the user may control the apparatus such that the vapor or aerosol passes through the bypass channel, and hence does not pass through any of the plurality of material elements 624, 626, 628.

In one example of flow regulation, referring again to FIG. 5, the flow from the first portion 596 of the outer cavity 594 of the material element 526 into the central cavity 592 of the material element 526 may be regulated. Alternatively or additionally, the flow from the central cavity 592 of the material element 526 to the second portion 598 of the outer cavity 594 of the material element 526 may be regulated. In one example, similar regulation may be applied to each of the material elements 524, 526, 528 to allow a user to control the flow of vapor or aerosol through each of the material elements 524, 526, 528, independently.

Other configurations of flow of the vapor or aerosol from the cartridge 104 etc., through the plurality of material elements 124, 126, 128 etc., and out for inhalation by a user may also be used. For example, the vapor or aerosol may flow out radially from the centre of a material element 124, 126, 128 etc. to an extremity of the material element 124, 126, 128, etc. In a similar example, the vapor or aerosol may flow in radially from an extremity of the material element 124, 126, 128, etc., to the center of the material element 124, 126, 128, etc.

Figure 7:
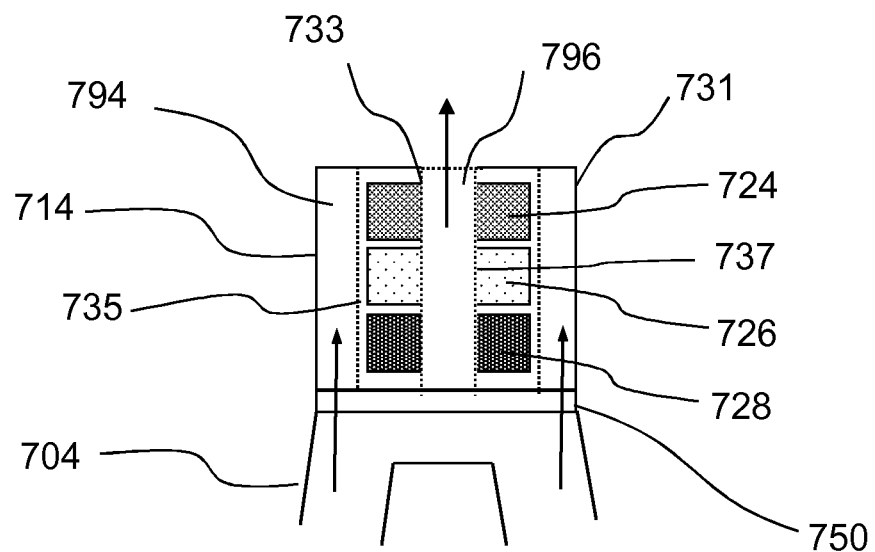
FIG. 7 shows a schematic cross-section of an exemplary receptacle.

FIG. 7 illustrates schematically a cross-section of an example receptacle 714 received in a receiving portion 750 of a cartridge 704 wherein the vapor flows radially through the material elements 724, 726, 728. The cartridge 704 shown in FIG. 7 may be used, for example, in apparatus 1 shown in FIG. 1, for example, instead of the cartridge 104 shown in FIG. 1. For brevity, features that do not differ from those features already described with reference to FIGS. 1-5 are not shown in FIG. 7 and will not be described again.

Referring to FIG. 7, the receptacle 714 comprises an outer portion 731 and an inner portion 733. The outer portion 731 is annular in shape, and allows for a plurality of material elements 724, 726, 728 to be received therein. The inner portion 733 is cylindrical in shape, and is placed centrally of the outer portion 731, i.e. coaxially with the outer portion 731. In order to be placed in the receptacle 714 therefore, each of the plurality of material elements 724, 726, 728 are also annular in shape, such that the inner portion 733 of the receptacle 714 is passed through a central hole (not shown) in each of the plurality of material elements 724, 726, 728. The plurality of material elements 724, 726, 728 may be received in the receptacle 714 in an ordered arrangement. For example, the plurality of material elements 724, 726, 728 may be manually inserted into the receptacle 714 in an ordered positional arrangement. The dimensions of the material elements 724, 726, 728 relative to the receptacle 714 may be such that, once inserted, the ordered positional arrangement of the material elements 724, 726, 728 may remain fixed unless a manual reordering of one or more of the material elements 124, 126, 128 is performed. The outer portion 731 of the receptacle 714 comprises a first cavity 794 within the body of the outer portion 731 itself. The first cavity 794 opens at one end of the outer portion 731 to allow vapor or aerosol to flow into (or out of) the cavity 794. An inner wall 735 of the outer portion 731 is arranged so as to allow vapor or aerosol to pass there through, but to prevent solid material passing there through. For example the inner wall 735 may be perforated or the like. The inner portion 733 of the receptacle 714 comprises a second cavity 796 that is open at one end to allow vapor or aerosol to flow out of (or into) the second cavity 796. An outer wall 737 of the inner portion 733 of the receptacle 714 is arranged so as to allow vapor or aerosol to pass there through but to prevent solid material passing there through.

In the example illustrated in FIG. 7, as shown by the arrows in the figure, vapor or aerosol flows from the cartridge 704 into the first cavity of the outer portion 731 of the receptacle 714. The vapor or aerosol then flows through the inner wall 735 of the outer portion 731 of the receptacle, inwardly, radially, and simultaneously through the plurality of material elements 724, 726, 728, through the outer wall 737 of the inner portion 733 of the receptacle 714, and into the second cavity 796 of the inner portion 722. The vapor or aerosol then exits the second cavity 796 of the inner portion 722 for inhalation by a user.

Although in the example illustrated in FIG. 7, the vapor flows inwardly through the material elements 724, 726, 728 from the outer portion 731 to the inner portion 733 of the receptacle 714, in other examples the receptacle 714 may be arranged such that the vapor or aerosol flows outwardly through the material elements 724, 726, 728 for inhalation by a user.

Each material element 724, 726, 728 may be separated by an impermeable membrane (not shown), i.e. a membrane impermeable to gas, vapor, aerosol, solid, liquid, or the like. This impermeable membrane (not shown) may, for example, take the form of a thin annular disc (not shown) or the like placed over the inner portion 733 of the receptacle 714, and separating each material element 724, 726, 728 from another of the plurality of material elements 724, 726, 728. For example, in the example of FIG. 7, a second material element 726 is stacked on top of a first material element 728, and a third material element 724 is stacked on top of the second material element 726. In this example, there may be an impermeable membrane (not shown) placed between the first material element 728 and the second material element 726, and another impermeable membrane between the third material element 724 and the second material element 726. The impermeable membrane prevents mixing of the material elements 724, 726, 728 with one another. The impermeable membrane (not shown) may be, for example, made from any suitably impermeable material, for example, plastic, rubber or the like.

In the example illustrated in FIG. 7, the annular material elements 724, 726, 728 are received in a receptacle 714. However, in other examples, the material elements may comprise annular self-supporting containers for containing solid material, each of which can be received in (and removably connected to) the receiving portion of the cartridge, and removably connectable to each other.

Figure 8:
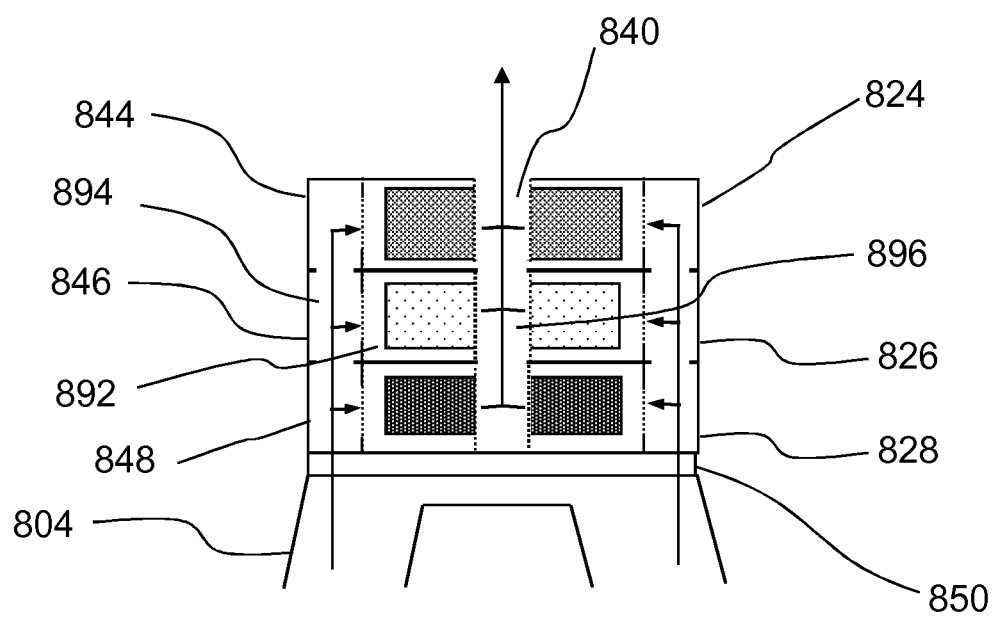
FIG. 8 shows a schematic cross-section of some exemplary containers.

FIG. 8 illustrates a schematic cross section of an example plurality of annular material elements 824, 826, 828 comprising respective annular containers 844, 846, 848 for containing respective solid material 864, 866, 868. In the example of FIG. 8, aerosol or vapor drawn from a cartridge 804 flows, in separate streams, radially through each material element 824, 826, 828. The cartridge 804 may be, for example, used in apparatus 1 shown in FIG. 1, for example, in place of the cartridge 104 shown in FIG. 1. For brevity, features that do not differ from those features already described with reference to FIGS. 1-7 are not shown in FIG. 8 and will not be described again.

Referring to FIG. 8, the annular containers 844, 846, 848 are connected together and are received in and connected to a receiving portion 850 of the cartridge 804. Each of the containers 844, 846, 848 are basically the same, except that (in this example) they contain different solid materials, although of course it will be appreciated that this need not be the case and instead, for example, two or more of the containers 844, 846, 848 may contain the same solid or contain solid materials with the same or similar properties (e.g. flavor, aroma, etc.). Each container 844, 846, 848, for example container 846, comprises an inner annular cavity 892 for containing solid material, and an outer annular cavity 894 surrounding the inner annular cavity 892. The inner annular cavity 892 itself surrounds an inner cylindrical cavity 896. The outer annular cavity 894 and the inner annular cavity 892 are separated by a permeable retainer that allows vapor or aerosol, but not solid material, to pass there through. Similarly, the inner annular cavity 892 and the inner cylindrical cavity 896 are separated by a permeable retainer that allows vapor or aerosol, but not solid material, to pass there through. In the example illustrated in FIG. 8, the containers 844, 846, 848 are connected so as to be stacked one on top of the other. When the annular containers 844, 846, 848 are connected together, the inner cylindrical cavity 896 of each annular container 844, 846, 848 combine to form a central cylindrical cavity 840 along their longitudinal axis along which vapor or aerosol can flow. Also, when the annular containers 844, 846, 848 are connected together, the outer annular cavity 894 of each annular container 844, 846, 848 connect together so that vapor or aerosol can flow there between. However, when the annular containers 844, 846, 848 are connected together, the inner annular cavity 896 of each container 844, 846, 848 do not connect together, and are separated by an impermeable membrane that does not allow vapor or aerosol or solid material to pass there through.

As shown by the arrows in the figure, according to the above described arrangement, vapor or aerosol flows from the cartridge 804 into the outer annular cavity 894 of each of the containers 844, 846, 848. For each of the containers 844, 846, 848, an individual stream of the vapor or aerosol flows radially inwardly from the outer annular cavity 894, through the inner annular cavity 892 (and hence the solid material contained therein), to the inner cylindrical cavity 896. The separate vapor or aerosol streams from each of containers 844, 846, 848 combine in the central cylindrical cavity 840 and then exit the central cylindrical cavity for inhalation by a user.

Although in the example illustrated in FIG. 8, the vapor flows radially inwardly from the outer annular cavity 894, through the inner annular cavity 892 (and hence the solid material contained therein), to the inner cylindrical cavity 896, in other examples the containers 844, 846, 848 and/or the receiving portion 850 and/or the cartridge 804 may be arranged such that the vapor or aerosol flows radially outwardly from the inner cylindrical cavity 896, through the inner annular cavity 892 (and hence the solid material contained therein), to the outer annular cavity 894 and then on for inhalation by a user. In this example, it will be appreciated that the outer annular cavity 894 may be omitted, and the vapor or aerosol may simply flow out the inner annular cavity 892 for inhalation by the user.

Although the examples above referred to use of the plurality of material elements 124, 126, 128, etc., with a cartridge 104 etc., it will be readily appreciated that there are many configurations of so called e-cigarettes (some of which not having cartridges as such, but rather, for example, refillable chambers integral to the apparatus 1) and that the above examples may also be applied to these other configurations. Indeed, the flow of a vapor or aerosol through a plurality of material elements 124, 126, 128, etc., as described above may be independent of the configuration of the source of that vapor or aerosol.

Figure 9:
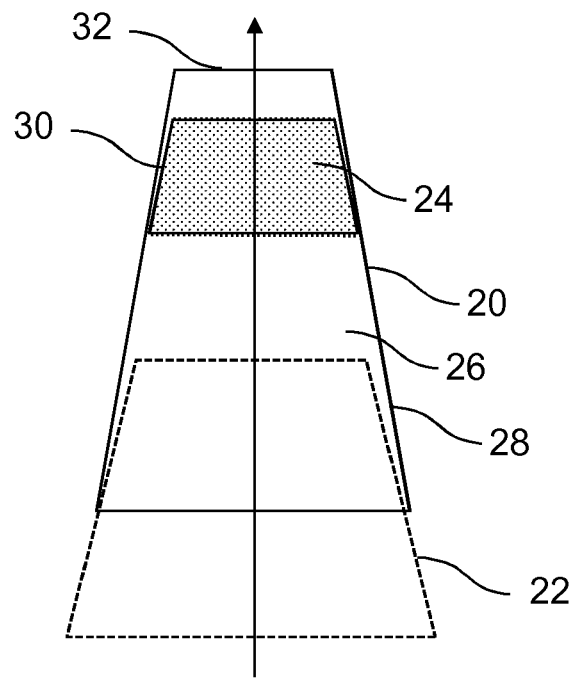
FIG. 9 shows a schematic cross-section of an exemplary cap.

FIG. 9 shows a schematic cross section of an exemplary cap 20 placed over a mouthpiece 22 of an apparatus for generating an inhalable medium such as. The apparatus may be, for example, an e-cigarette similar to or the same as apparatus 1 described above, or indeed any e-cigarette.

The cap 20 comprises a connecting portion 28 for connecting to the mouthpiece 22 and a receiving portion 30 for receiving solid material 24. The connecting portion 28 is shaped so as to allow the connecting portion 28 to form a seal, for example, an air tight seal, between the cap 20 and any one of a plurality of mouthpieces 22. The connecting portion 28 allows the cap 20 to be connected to a mouthpiece 22 such that the cap 20 does not become detached from the mouthpiece 22 for example when a user draws on the cap 20 in use to inhale an inhalable medium, but does become detached from the mouthpiece 22 for example when a user intentionally pulls the cap 20 away from the mouthpiece 22 so as to remove it. In this example, the cap 20 is frustroconical in shape. The connecting portion 28 of the cap 20 comprises a frustroconical recess 26 for receiving the mouthpiece 22 therein and forming a seal between the cap 20 and the mouthpiece 22, for example an airtight seal. The connecting portion 28 may be made, for example, from rubber, or plastic, or any material suitable for forming an airtight seal between the connecting portion 28 and the mouthpiece 22. The connecting portion 28 is such so as to allow the cap 20 to be removable from the mouthpiece 22.

The receiving portion 30 may have received therein a solid material, such as tobacco, or any material that may impart flavor or other constituents to vapor or aerosol passing there through. The receiving portion may be integral to the cap 20, and the solid material 24 therein may not be accessible or replaceable by a user. The cap 20 may therefore be disposable. Alternatively, the receiving portion 30 may be arranged so as to allow a user access to the solid material 24, and hence allow a user to add, remove, or exchange the solid material 24 received therein. The cap 20 may therefore be reusable. The receiving portion 30 is arranged so as to allow vapor or aerosol emanating from the mouthpiece 22 to pass from the recess 26, through the solid material 32, and out of a first end 32 of the cap 20 for inhalation by a user (as illustrated by the arrow in FIG. 9). For example, the receiving portion may comprise a container with perforated walls (not shown) that allow vapor or aerosol to pass there through, but not allow the solid material 24 to pass there through. The receiving portion may have received therein a plurality of discrete solid material elements (not shown), such as self-supporting portions of solid material, or solid material contained in a container arranged so as to allow vapor or aerosol to pass there through, but not to allow the solid material to pass there through.

Different caps 20 that each contain a different solid material or plurality of solid material elements (and hence each imparting different flavors or other properties, such as nicotine content, to the vapor or aerosol passing there through) may be available, hence allowing a user to easily customize their experience. Multiple caps 20 may be placed one on top of the other (not shown), each forming an airtight seal with adjacent caps, so as to allow the flavor or other constituent properties imparted by the caps to the vapor or aerosol passing there through to be easily combined.

Figure 10:
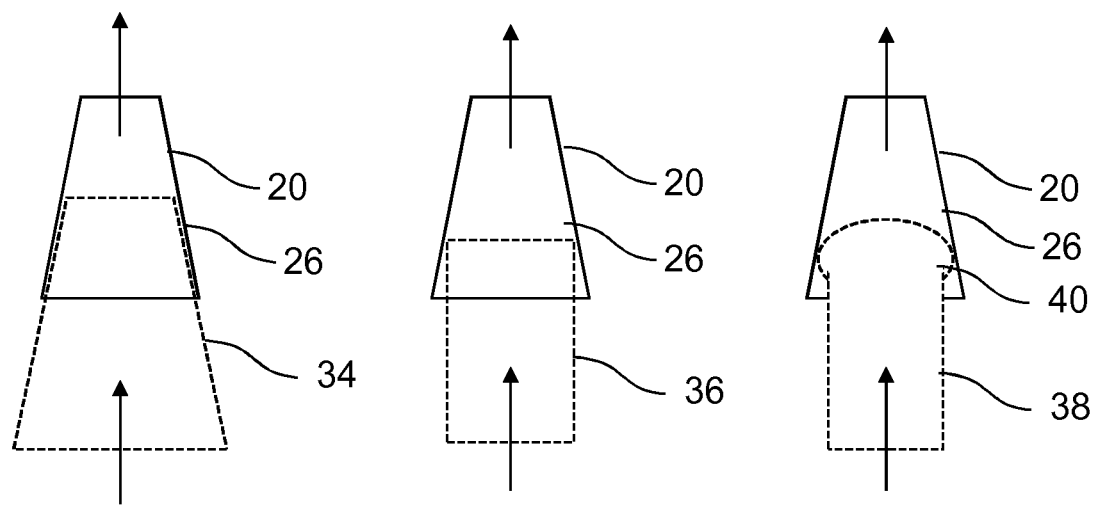
FIG. 10 shows schematic cross-sections of an exemplary cap connected to a variety of mouthpieces.

The frustroconical recess 26 of the connecting portion 28 of the cap 20 allows the cap 20 to be connected universally to any one of a variety of different shapes of mouthpiece 22 or a variety of mouthpieces of the same general shape but of different sizes. FIG. 10 illustrates schematically how an exemplary cap 20 with a frustroconical recess 26 may be connected so as to form a seal, for example an air tight seal, with a mouthpiece 34 that itself is conical or frustroconical in shape, with a mouthpiece 36 that is cylindrical in shape, and with a mouthpiece 38 with a bulbous end 40. Essentially the decreasing diameter of the frustroconical recess 26 from the opening of the recess 26 towards the receiving portion 30 allows the cap 20 to be lowered (pushed) onto a mouthpiece 38 until the diameter of the mouthpiece matches the diameter of the recess 26, hence allowing a seal, for example an air tight seal, to be formed.

It will be appreciated that the recess 26 need not necessarily be frustroconical in shape, and may be instead any tapered recess in which the diameter of the recess 26 decreases from the opening of the recess 26 towards the receiving portion 30 of the cap 20, for example, a cone, a dome, a pyramid, a frustro-pyramid, or the like.

Figure 11:
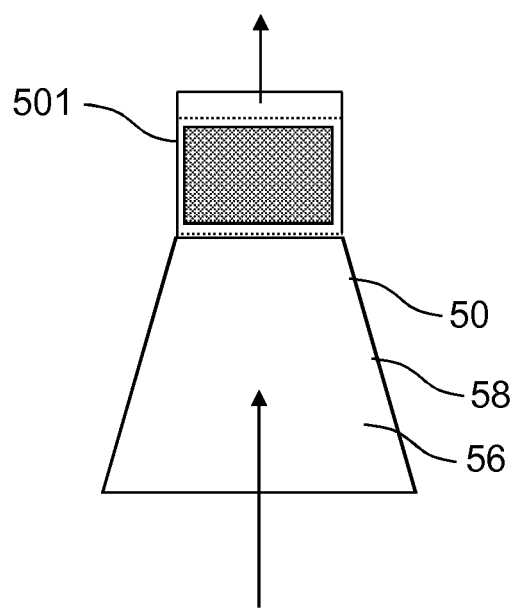
FIG. 11 shows a schematic cross-section of an exemplary cap.
Figure 12:
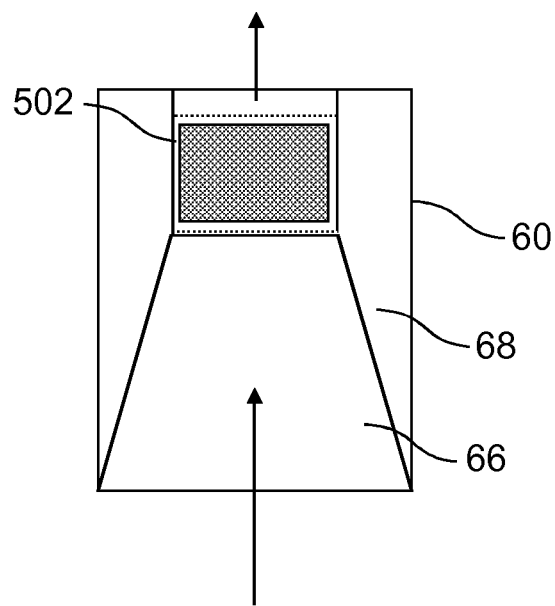
FIG. 12 shows a schematic cross-section of an exemplary cap.

Moreover, it will be appreciated that the cap 20 need not be frustroconical in shape. FIGS. 11 and 12 illustrate schematically cross sections of alternative caps 50, 60 that comprise a tapered recess (in this example a frustroconical recess), but are not in themselves frustroconical in shape.

Referring to FIG. 11, the cap 50 comprises connecting portion 56 and receiving portion 501. The receiving portion 501 is cylindrical in shape, and the connecting portion 56 is frustroconical in shape. The connecting portion 56 comprises a frustroconical recess 56 allowing the cap 50 to be placed on a mouthpiece (not shown) so as to form an airtight seal between the connecting portion 58 and the mouthpiece (not shown).

Referring to FIG. 12, the cap 60 comprises connecting portion 66 and receiving portion 601. The receiving portion 601 is cylindrical in shape, and the connecting portion 66 is cylindrical in shape. The connecting portion 66 comprises a frustroconical recess 56 allowing the cap 60 to be placed on a mouthpiece (not shown) so as to form an airtight seal between the connecting portion 68 and the mouthpiece (not shown).

A number of other variations and alternatives to the examples described above are possible.

For example, in some cases it may be possible for the plurality of solid material elements to be located, exclusively or additionally, in the mouthpiece of the apparatus (battery section, etc.) with which the cartridge described above is used.

As another example, the plurality of material elements may be selectively omitted from the receptacle, for example at the option of the user. This provides the user with more flexibility.

It is described above that the channel 116, 216, etc., is annular and completely surrounds the liquid container 132, 232, etc. In other examples, the channel is not annular and does not surround the liquid container 132, 232, etc. For example, there may be a single, substantially tubular channel or groove extending from the liquid container 132, 232, etc. As another example, there may be plural channels or grooves extending from the liquid container 132, 232, etc., one or more of which may be substantially tubular. Where there are plural channels, it is possible for the channels to lead to a separate one or more of the plurality of material elements.

In some of the examples above, the liquid container and the plurality of material elements or receptacle are arranged substantially in-line, along a longitudinal axis of the apparatus or cartridge. In other examples, the liquid container and the material elements or receptacle are arranged so as to at least partially overlap in the longitudinal direction of the apparatus or cartridge; in such examples, the liquid container and the material elements or receptacle may still be arranged generally in-line along the longitudinal axis of the apparatus or cartridge, or may be arranged side by side, or with one partially or completely inside the other. In yet other examples, the liquid container and the material elements or receptacle are arranged concentrically (either with the liquid container inside the material elements or receptacle or vice versa), and may be arranged to be entirely off-set with respect to each other along the longitudinal axis of the apparatus or cartridge, or overlapping, or one completely within the other.

The liquid can be a liquid that is volatilizable at reasonable temperatures, such as in the range of 100-300° C. or more particularly around 150-250° C., as that helps to keep down the power consumption of the apparatus with which the cartridge is used. Suitable materials include those conventionally used in e-cigarette devices, including for example propylene glycol and glycerol (also known as glycerine). Also as described in relation to the examples above, the solid material is a material that may be used to impart a flavor (or other constituent) to the aerosol or vapor produced from the liquid as the aerosol or vapor passes through the material. For example, the material may comprise constituents that impart cooling sensations, heating sensations, nutraceutical benefits, stimulating benefits or produce or induce any other sensation or benefit in the user. The material may for example consist of or comprise tobacco. As the aerosol or vapor passes through and over the tobacco material, the aerosol or vapor entrains organic and other compounds or constituents from the tobacco material that lend tobacco its organoleptic properties, thus imparting the flavor to the aerosol or vapor as it passes to the mouthpiece. Materials other than tobacco may be used to impart different flavors to the aerosol or vapor stream. For example, materials other than tobacco may be blended with tobacco, or blends of other materials such as, for example, vanilla pods, star anise, mint leaves, other herbs, and the like. Flavorants may be included in the material or in the liquid or both.

In any of the examples described above, an apparatus controller may control operation of the apparatus as a whole. The controller for example may cause the heater to be powered as and when required and switch off the heater when heating is not required. Operation of the heater may be controlled so that the liquid and/or material is heated to an optimum temperature. Particular considerations include ensuring that the solid material does not burn, ensuring that adequate vaporization of the liquid is achieved, ensuring that the vaporized liquid or aerosol is at an appropriate temperature to liberate compounds from the solid material, and ensuring that the vapor or aerosol that reaches the user is at a comfortable and safe temperature. A puff detector, a device which is known per se, may be provided to signal to the controller when the heating elements need to be energized. The apparatus may also have one or more filters for filtering the vapor or aerosol before it reaches the user, cooling arrangements for cooling the vapor or aerosol before it reaches the user, insulation internally of the apparatus to protect the user from the heat generated inside the housing, etc.

Heating of the material may encourage release of the constituents of the solid material into the vapor or aerosol passing there through. In use, the material may be heated by the vapor or aerosol that passes through the solid material. Alternatively or additionally, the solid material may be heated using a dedicated heater, for example an electro-resistive heater or an induction heater separate to the heater that heats the liquid. The use of an induction heater allows the material to be heated quickly, such that, for example, the solid material can be heated to a sufficient temperature to encourage release of constituents thereof within the duration of a draw of the user. The dedicated heater may, for example, surround the solid material or the receptacle/container in which it is received. For example, particularly in the case that the solid material is tobacco, the tobacco, or at least the surface of the tobacco, can be heated to a temperature of between around 190° C. to 210° C., such as around 200° C., so as to ensure that an adequate or appropriate amount of the compounds are released from the tobacco. The heating of the material may comprise pre-heating. In the case of pre-heating, the material, particularly in the case of tobacco, may be pre-heated to a temperature in the range of around 100 to 150° C. It will be appreciated however that other temperatures may be used. For example, the solid material, or at least the tobacco in contact with the heater, may be heated to a temperature above 210° C., such as up to around 230° C. or 240° C. or so and even as high as 290° C. or so. The amount of tobacco present may be for example in the range 50 to 300 mg or so. A most suitable value for the amount of tobacco may be for example in the range 50 to 150 mg, with 130 mg being a value that is currently found to be particularly suitable in some applications. In a typical example, the amount of tobacco that is heated per operation of the apparatus (i.e. per puff) may be in the corresponding range of around 8 to 50 mg. The function of dedicated heater may be independently controllable by the user from other functions of the overall apparatus, for example to allow the user to control whether or not, or to what extent, the material is pre-heated or heated by the dedicated heater.

In use, the liquid may be heated to a temperature of between around 100-300° C. or more particularly around 150° C. to 250° C. Suitable materials 14, etc., include materials that provide volatilized components upon heating, typically in the form of an aerosol. Suitable solid materials include any tobacco-containing material and may, for example, include one or more of tobacco per se, different varieties of tobacco, tobacco derivatives, pelletized tobacco, extruded tobacco, expanded tobacco, reconstituted tobacco, ground tobacco, tobacco extract, homogenized tobacco or tobacco substitutes. In the case of tobacco, the solid material may be in the form of a rod of tobacco, a pod or plug of tobacco, loose tobacco, agglomerates, etc., and may be in relatively dry form or in relatively moist form for example. The tobacco may have been modified, for example chemically modified, for example had its pH modified so as to promote the release of selected constituents of the tobacco such as nicotine. Suitable solid materials may include other, non-tobacco, products, which, depending on the product, may or may not contain nicotine. In some examples, the receptacle or container for the solid material is transparent, so that the user can see the contents (i.e. the solid material) in use, which is appealing to some users. The tobacco rod may be formed using a transparent material as a wrapping material, again so that the user can see the tobacco. A particularly suitable material is NatureFlex™, a biodegradable film made from renewable raw materials by Innovia Films Limited.

As used herein, the terms "flavor" and "flavorant" refer to materials which, where local regulations permit, may be used to create a desired taste or aroma in a product for adult consumers. They may include extracts (e.g., licorice, hydrangea, Japanese white bark magnolia leaf, chamomile, fenugreek, clove, menthol, Japanese mint, aniseed, cinnamon, herb, wintergreen, cherry, berry, peach, apple, Drambuie, bourbon, scotch, whiskey, spearmint, peppermint, lavender, cardamom, celery, cascarilla, nutmeg, sandalwood, bergamot, geranium, honey essence, rose oil, vanilla, lemon oil, orange oil, cassia, caraway, cognac, jasmine, ylang-ylang, sage, fennel, piment, ginger, anise, coriander, coffee, or a mint oil from any species of the genus Mentha), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, oil, liquid, or powder. For example, a liquid, oil, or other such fluid flavorant may be impregnated in a porous solid material so as to impart flavor and/or other properties to that porous solid material. As such, the liquid or oil is a constituent of the solid material in which it is impregnated.

Each discrete material element may have, for example, a volume in the range of 100 mm$^3$ to 1200 mm$^3$, such as in the range of 150 mm$^3$ to 800 mm$^3$ or 200 mm$^3$ to 800 mm$^3$, and more particularly in the range 150 mm$^3$ to 500 mm$^3$.

Each discrete material element may have, for example, a mass in the range of 20 mg to 600 mg, such as in the range of 40 mg to 300 mg and more particularly in the range 60 mg to 200 mg.

Although in the above examples, the material was described as being a solid material or material in solid form, this need not necessarily be the case. In other examples, the material may be a fluid, such as a liquid.

The above embodiments are to be understood as illustrative examples of the invention. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. An apparatus for generating an inhalable medium, the apparatus comprising:
a liquid container for holding a liquid;
a heater for volatilizing the liquid held in the liquid container;
a stack comprising a plurality of discrete material elements, wherein each discrete material element of the plurality of discrete material elements is abutted with another of the plurality of discrete material elements; and
a receiving portion for receiving the stack comprising the plurality of discrete material elements,
the apparatus being arranged such that in use the liquid volatized by the heater passes, in the form of at least one of a vapor or an aerosol, through a material of one or more of the plurality of discrete material elements received by the receiving portion in use thereby to entrain one or more constituents of the one or more of the plurality of discrete material elements to produce the inhalable medium;
wherein the receiving portion comprises a receptacle having received therein said stack comprising said plurality of discrete material elements, the receiving portion having a first permeable retainer at an upstream end of the receptacle and a second permeable retainer at a downstream end of the receptacle to prevent passage of solid material through the receptacle and into a mouthpiece; and
wherein the first permeable retainer and the second permeable retainer cooperatively retain the plurality of discrete material elements within the receptacle, and wherein the second permeable retainer is removable to allow access to the plurality of discrete material elements, and wherein one of the plurality of discrete material elements is exchangeable for another discrete material element.

2. A cartridge for use with an apparatus for generating an inhalable medium, the cartridge comprising:
a container for holding a liquid;
a stack comprising a plurality of discrete material elements, wherein each discrete material element of the plurality of discrete material elements is abutted with another of the plurality of discrete material elements; and
a receiving portion for receiving the stack comprising the plurality of discrete material elements, the cartridge being arranged such that, in use, the liquid exiting the container can flow, in the form of at least one of a vapor or an aerosol, through a material of one or more of the plurality of discrete material elements received by the receiving portion in use, thereby to entrain one or more constituents of the one or more of the plurality of discrete material elements to produce the inhalable medium;
wherein the receiving portion is a receptacle having received therein said stack comprising a said plurality of discrete material elements, wherein the receptacle comprises a first permeable retainer at an upstream end of the receptacle and a second preamble retainer at a downstream end of the receptacle to retain the plurality of discrete material elements and to prevent passage of solid material through the receptacle, and wherein the second permeable retainer is removable to allow access to the plurality of discrete material elements; and
wherein one of the plurality of discrete material elements is exchangeable for another discrete material element.

3. The cartridge according to claim 2, wherein the container and the receiving portion form an integral unit.

4. The cartridge according to claim 2, wherein the receiving portion is connectable to, and removable from, the liquid container.

5. The cartridge according to claim 2, the cartridge being arranged such that, in use, the liquid exiting the container passes, in the form of at least one of the vapor or the aerosol, sequentially through each of the plurality of discrete material elements received by the receiving portion in use.

6. The cartridge according to claim 2, wherein the retainer is arranged so as to allow the vapor or the aerosol to pass there through.

7. The cartridge according to claim 2, wherein the receiving portion is arranged to allow one or more of:
changing an order of one or more of the plurality of discrete material elements received by the receiving portion in use;
adding one or more discrete material elements to the receiving portion; and
removing one or more of the discrete material elements from the receiving portion.

8. The cartridge according to claim 2, wherein the plurality of discrete material elements are in an ordered arrangement.

9. The cartridge according to claim 2, wherein each of the plurality of discrete material elements is the same.

10. The cartridge according to claim 2, wherein one of the plurality of discrete material elements has a property different to that of another of the plurality of discrete material elements.

11. The cartridge according to claim 2, wherein each one of the plurality of discrete material elements has a property different to that of each other one of the plurality of discrete material elements.

12. The cartridge according to claim 10, wherein the property is one of aroma or flavor.

13. The cartridge according to claim 2, wherein the plurality of discrete material elements are stacked one on top of the other.

14. The cartridge according to claim 2, wherein one or more of the plurality of discrete material elements comprises material in solid form.

15. The cartridge according to claim 14, wherein the material in solid form is or comprises tobacco.

16. The cartridge according to claim 14, wherein the material in solid form is or comprises a flavored solid material.

17. An apparatus comprising the cartridge according to claim 2, further comprising a heater for volatilizing the liquid held in the container.

18. A system for generating an inhalable medium, the system comprising:
a heater for volatilizing a liquid; and
a cartridge comprising:
a container for holding the liquid,
a stack comprising a plurality of discrete material elements, wherein each discrete material element of the plurality of discrete material elements is abutted with another of the plurality of discrete material elements, and a receiving portion for receiving the stack comprising the plurality of discrete material elements, the heater and the cartridge being arranged such that, in use, the liquid volatized by the heater and exiting the container can flow, in the form of at least one of a vapor or an aerosol, through a material of one or more of the plurality of discrete material elements received by the receiving portion in use, thereby to entrain one or more constituents of the one or more of the plurality of discrete material elements to produce the inhalable medium;

wherein the receiving portion is a receptacle having received therein said stack comprising a said plurality of discrete material elements wherein the receptacle comprises a first permeable retainer at an upstream end of the receptacle and a second permeable retainer at a downstream end of the receptacle to retain the plurality of discrete material elements and to prevent passage of solid material through the receptacle and into a mouthpiece, and wherein the second permeable retainer is removable to allow access to the plurality of discrete material elements; and wherein one of the plurality of discrete material elements is exchangeable for another discrete material element.

* * * * *